(12) United States Patent
Greiner et al.

(10) Patent No.: US 8,938,297 B2
(45) Date of Patent: Jan. 20, 2015

(54) IMPLANTABLE ELECTROACUPUNCTURE DEVICE AND METHOD FOR TREATING CARDIOVASCULAR DISEASE

(71) Applicant: Valencia Technologies Corporation, Valencia, CA (US)

(72) Inventors: Jeffrey H. Greiner, Valencia, CA (US); David K. L. Peterson, Valencia, CA (US); Chuladatta Thenuwara, Castaic, CA (US)

(73) Assignee: Valencia Technologies Corporation, Valencia, CA (US)

( * ) Notice: Subject to any disclaimer, the term of this patent is extended or adjusted under 35 U.S.C. 154(b) by 14 days.

(21) Appl. No.: 13/622,497

(22) Filed: Sep. 19, 2012

(65) Prior Publication Data

US 2014/0214111 A1    Jul. 31, 2014

Related U.S. Application Data

(60) Provisional application No. 61/626,339, filed on Sep. 23, 2011, provisional application No. 61/606,995, filed on Mar. 6, 2012, provisional application No. 61/609,875, filed on Mar. 12, 2012, provisional application No. 61/672,257, filed on Jul. 16, 2012, provisional application No. 61/672,661, filed on Jul. 17, 2012, provisional application No. 61/674,691, filed on Jul. 23, 2012, provisional application No. 61/676,275, filed on Jul. 26, 2012.

(51) Int. Cl.
*A61N 1/05* (2006.01)
*A61N 1/362* (2006.01)

(52) U.S. Cl.
CPC ...................................... *A61N 1/362* (2013.01)

USPC .......................................................... 607/30

(58) Field of Classification Search
USPC ........................................................ 607/2, 30
See application file for complete search history.

(56) References Cited

U.S. PATENT DOCUMENTS

| | | |
|---|---|---|
| 4,528,072 A | 7/1985 | Kurosawa |
| 4,535,784 A | 8/1985 | Rohlicek |
| 4,566,064 A | 1/1986 | Whitaker |

(Continued)

OTHER PUBLICATIONS

Longhurst, J.C., "Central and Peripheral Neural Mechanisms of Acupuncture in Myocardial Ischemia", International Congress Series 1238 (2002) 79-87.

(Continued)

*Primary Examiner* — Joseph Dietrich
(74) *Attorney, Agent, or Firm* — Bryant R. Gold

(57) ABSTRACT

An implantable electroacupuncture device (IEAD) treats heart failure, coronary artery disease, myocardial ischemia or angina through application of stimulation pulses applied at acupoints GV20 and/or EXHN3. The IEAD comprises an implantable, coin-sized, self-contained, leadless electroacupuncture device having at least two electrodes attached to an outside surface of its housing. The device generates stimulation pulses in accordance with a specified stimulation regimen. Power management circuitry within the device allows a primary battery, having a high internal impedance, to be used to power the device. The stimulation regimen generates stimulation pulses during a stimulation session of duration T3 minutes applied every T4 minutes. The duty cycle, or ratio of T3/T4, is very low, no greater than 0.05. The low duty cycle and careful power management allow the IEAD to perform its intended function for several years.

7 Claims, 19 Drawing Sheets

(56) References Cited

U.S. PATENT DOCUMENTS

| | | | |
|---|---|---|---|
| 5,195,517 A | 3/1993 | Chen | |
| 5,199,428 A | 4/1993 | Obel | |
| 5,211,175 A | 5/1993 | Gleason | |
| 5,250,068 A | 10/1993 | Ideguchi | |
| 5,251,637 A | 10/1993 | Shalvi | |
| 5,372,605 A | 12/1994 | Adams et al. | |
| 5,544,656 A | 8/1996 | Pitsillides | |
| 5,707,400 A | 1/1998 | Terry, Jr. | |
| 5,891,181 A | 4/1999 | Zhu | |
| 6,006,134 A | 12/1999 | Hill | |
| 6,178,352 B1 | 1/2001 | Gruzdowich | |
| 6,393,324 B2 | 5/2002 | Gruzdowich | |
| 6,522,926 B1 | 2/2003 | Kieval | |
| 6,658,298 B2 | 12/2003 | Gruzdowich | |
| 6,735,475 B1 | 5/2004 | Whitehurst | |
| 6,839,596 B2 | 1/2005 | Nelson | |
| 6,950,707 B2 | 9/2005 | Whitehurst | |
| 6,978,174 B2 | 12/2005 | Gelfand | |
| 7,003,352 B1 | 2/2006 | Whitehurst | |
| 7,136,701 B2 | 11/2006 | Greatbatch | |
| 7,162,303 B2 | 1/2007 | Levin | |
| 7,171,266 B2 | 1/2007 | Gruzdowich | |
| 7,203,548 B2 | 4/2007 | Whitehurst | |
| 7,292,890 B2 | 11/2007 | Whitehurst | |
| 7,321,792 B1 | 1/2008 | Min et al. | |
| 7,373,204 B2 | 5/2008 | Gelfand | |
| 7,440,806 B1 | 10/2008 | Whitehurst | |
| 7,620,451 B2 | 11/2009 | Demarais | |
| 7,962,219 B2 | 6/2011 | Jaax | |
| 2003/0158588 A1 | 8/2003 | Rizzo | |
| 2003/0187485 A1 | 10/2003 | Sturman | |
| 2003/0195583 A1* | 10/2003 | Gruzdowich et al. | 607/45 |
| 2005/0107832 A1 | 5/2005 | Bernabei | |
| 2005/0228460 A1 | 10/2005 | Levin | |
| 2005/0234533 A1 | 10/2005 | Schulman | |
| 2007/0005119 A1 | 1/2007 | Crohn | |
| 2007/0255319 A1 | 11/2007 | Greenberg | |
| 2007/0265680 A1 | 11/2007 | Liu | |
| 2009/0210026 A1 | 8/2009 | Solberg | |
| 2009/0292341 A1 | 11/2009 | Parramon et al. | |
| 2010/0069992 A1 | 3/2010 | Aghassian et al. | |
| 2010/0211132 A1 | 8/2010 | Nimmagadda | |
| 2010/0324624 A1 | 12/2010 | Chang | |
| 2010/0327887 A1 | 12/2010 | Denison et al. | |
| 2011/0106220 A1 | 5/2011 | DeGiorgio | |
| 2011/0112603 A1 | 5/2011 | DeGiorgio | |
| 2011/0218589 A1 | 9/2011 | DeGiorgio | |
| 2011/0218590 A1 | 9/2011 | DeGiorgio | |
| 2012/0022612 A1 | 1/2012 | Littlewood et al. | |
| 2013/0041396 A1 | 2/2013 | Ryotokuji | |

OTHER PUBLICATIONS

Mannheimer, C. et al., "The Problem of Chronic Refractory Angina," European Heart Journal (2002) 23, 355-370.

Sanderson, J.E., "Electrical Neurostimulators for Pain Relief in Angina," British Heart Journal (1990) 63: 141-143.

Cheung, et al., "The Mechanism of Acpuncture Therapy and Clinical Case Studies", (Taylor & Francis, publisher) (2001) ISBN 0-415-27254-8. The Forward, Chapters 1-3, 5, 7, 8, 12 & 13.

Zhou W, Fu LW, Tjen-A-Looi SC, et al, "Afferent mechanisms underlying stimulation of modality-related modulation of acupuncture-related cardiovascular responses," J Appl Physiol 2005, 98:872-880.

Tjen-A-Looi SC, Li P, Longhurst JC. "Medullary substrate and differential cardiovascular responses during stimulation of specific acupoints," Am J Physiol Regul Integr Comp Physiol 2004, 287:R852-R862.

WHO Standard Acupuncture Point Locations in the Western Pacific Region, World Health Organization (WHO), Western Pacific Region, 2008 (updated and reprinted 2009), ISBN 978 92 9061 248 7. The Table of Contents, Forward (v-vi), General Guidelines for Acupuncture Point Locations (1-21), p. 151 & 154.

"Acupuncture." http://en.wikipedia.org/wiki/Acupuncture.

Zhou WY, Tjen-A-Looi SC, Longhurst JC, "Brain stem mechanisms underlying acupuncture modality-related modulation of cardiovascular responses in rats," J Apply Physiol 2005, 99;851-860.

"Electroacupuncture." http://en.wikipedia.org/wiki/Electroacupuncture.

"Acupuncture Today: Electroacupuncture". Feb. 1, 2004 (retrieved on-line Aug. 9, 2006 at http://www.acupuncturetoday.com/abc/electroacupuncture.php).

Gao, J. et al., "Acupuncture pretreatment protects heart from injury in rats with myocardial ischemia and reperfusion via inhibition of the B1-adrenoceptor signaling pathway," Life Sciences 80 (2007) 1484-1489.

Li, P. et al., "Reversal of Reflex-Induced Myocardial Ischemia by Median Nerve Stimulation: A Feline Model of Electroacupuncture," American Heart Association Circulation 1998; 97: 1186-1194.

Middlekauf HR, Yu JL, Hui K, et al.: "Acupuncture inhibits sympathetic activation during mental stress in advanced heart failure patients," J Cardiac Failure: 8:399-406 (2002).

Richter A, Herlitz J, Hjalmarson A: "Effect of acupuncture in patients with angina pectoris," Eur Heart J: 12:175-8 (1991).

Oka, T., Tsuda, Y., Suzuki S., Aji, R., Kaneya, S., & Fujino, T.: "Treatment of angina pectoris with acupuncture—role of 'Neiguan," Jpn. J. Oriental Med. 38: 85-88.

Kurono, Y., Egawa, M., Yano, T., & Shimoo, K: "The effect of acupuncture on the coronary arteries as evaluated by coronary angiography: a preliminary report," Am J Chin Med 30: 387-396 (2002).

Lin D., Lin Y., Hu J., Ruan X: "Effect of Electroacupuncture on Neiguan and Shenmen Points on heart function after coronary artery bypass grafting in coronary heart disease." Modern Journal of Integrated Traditional Chinese and Western Medicine: 18:2241-41. Abstract. (2009).

Li P, Pitsillides KF, Rendig SV et al.: "Reversal of reflex-induced myocardial ischemia by median nerve stimulation: a feline model of electroacupuncture," Circulation 97: 1186-94 (1998).

Liu XQ, Lu SQ, Luo L: "Influence of acupuncture on epicardial monophasic action potential in vivo in dog with myocardial infarction," Tianjin Journal of Traditional Chinese Medicine 22: 480-481 (2005).

Yang L, Yang Y., Wang Q., et al.: "Cardioprotective effects of electroacupuncture pretreatment on patients undergoing heart valve replacement surgery: a randomized controlled trial," Ann Thorac Surg 89: 781-6 (2010).

Ballegaard S, Jensen G, Pedersen F et al: "Acupuncture in severe, stable angina pectoris: a randomized trial," Acta Med Scand 220: 307-13 (1986).

Greiner, U.S. Appl. No. 61/626,339, filed Sep. 23, 2011.
Peterson, U.S. Appl. No. 61/606,995, filed Mar. 6, 2012.
Peterson, U.S. Appl. No. 61/609,875, filed Mar. 12, 2012.
Peterson, U.S. Appl. No. 61/672,257, filed Jul. 16, 2012.
Peterson, U.S. Appl. No. 61/672,661, filed Jul. 17, 2012.
Peterson, U.S. Appl. No. 61/674,691, filed Jul. 23, 2012.
Thenuwara, U.S. Appl. No. 61/676,275, filed Jul. 26, 2012.
Greiner, U.S. Appl. No. 13/598,582, filed Aug. 29, 2012.
Greiner, U.S. Appl. No. 13/598,575, filed Aug. 29, 2012.
Greiner, U.S. Appl. No. 13/622,653, filed Sep. 19, 2012.
Greiner, U.S. Appl. No. 13/630,522, filed Sep. 28, 2012.
Greiner, U.S. Appl. No. 13/630,322, filed Sep. 28, 2012.

* cited by examiner

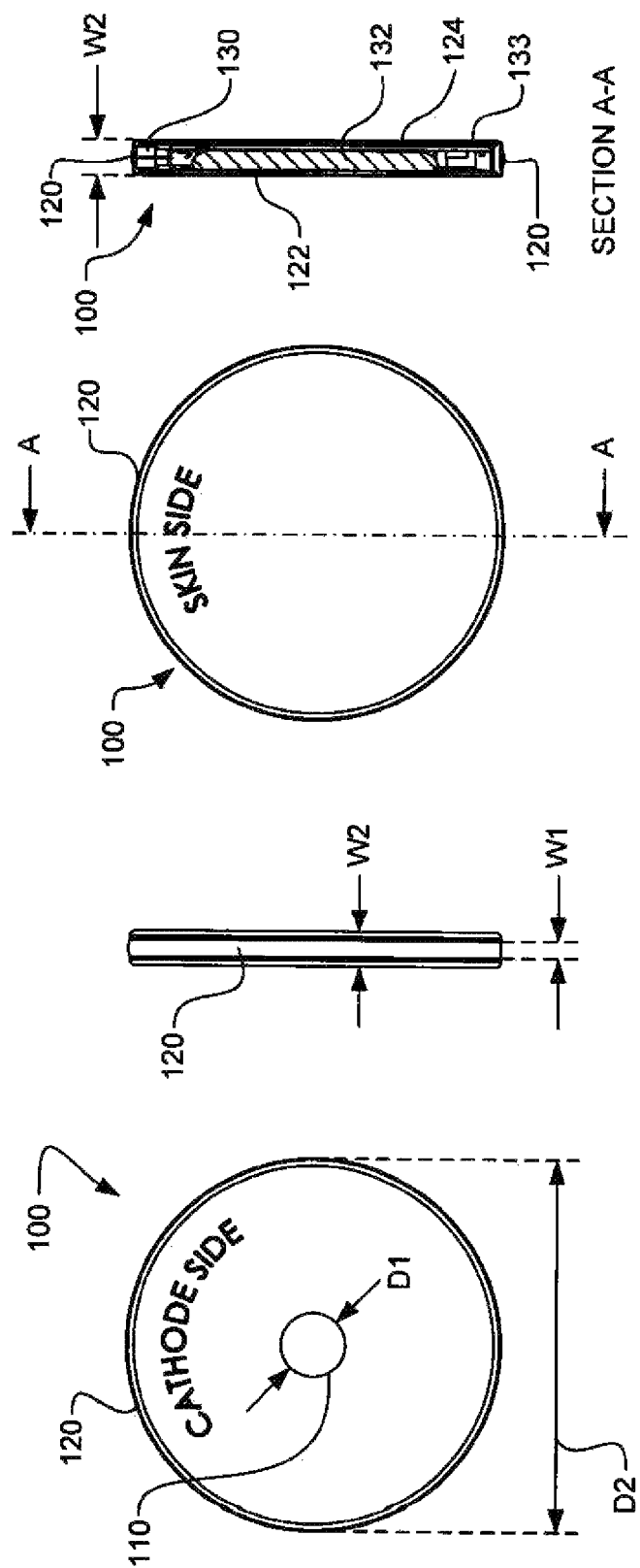

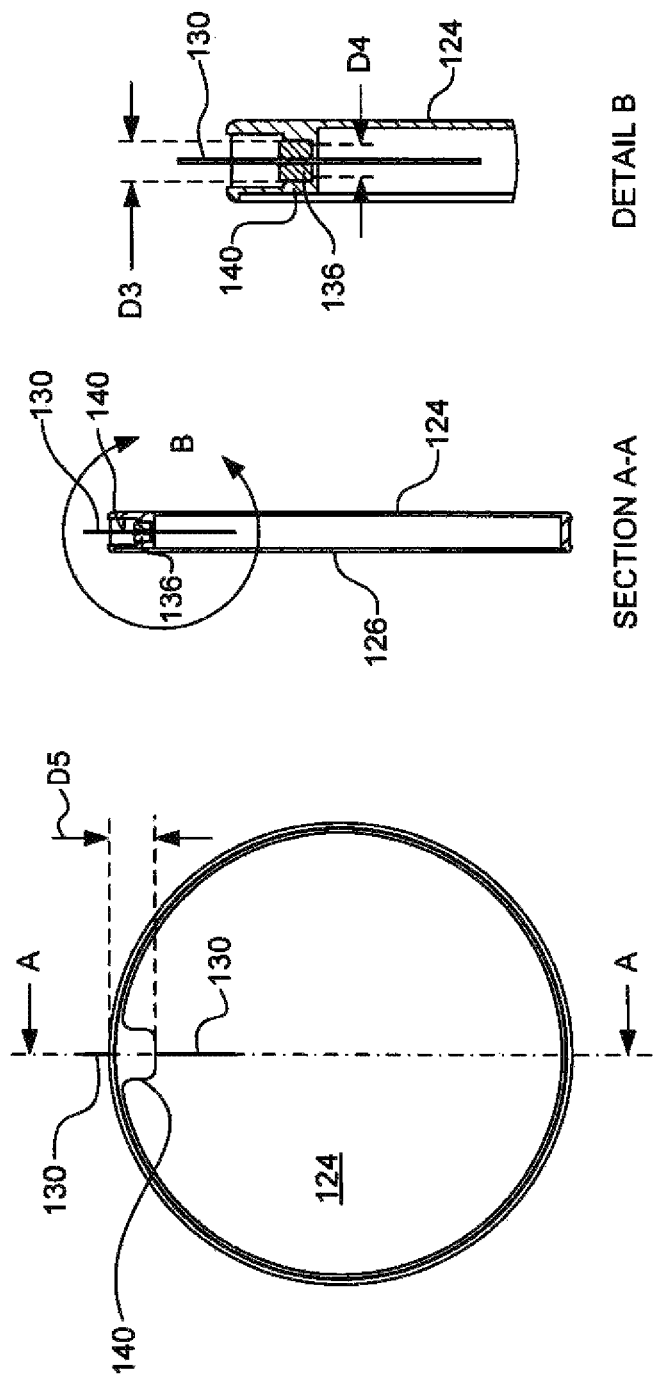

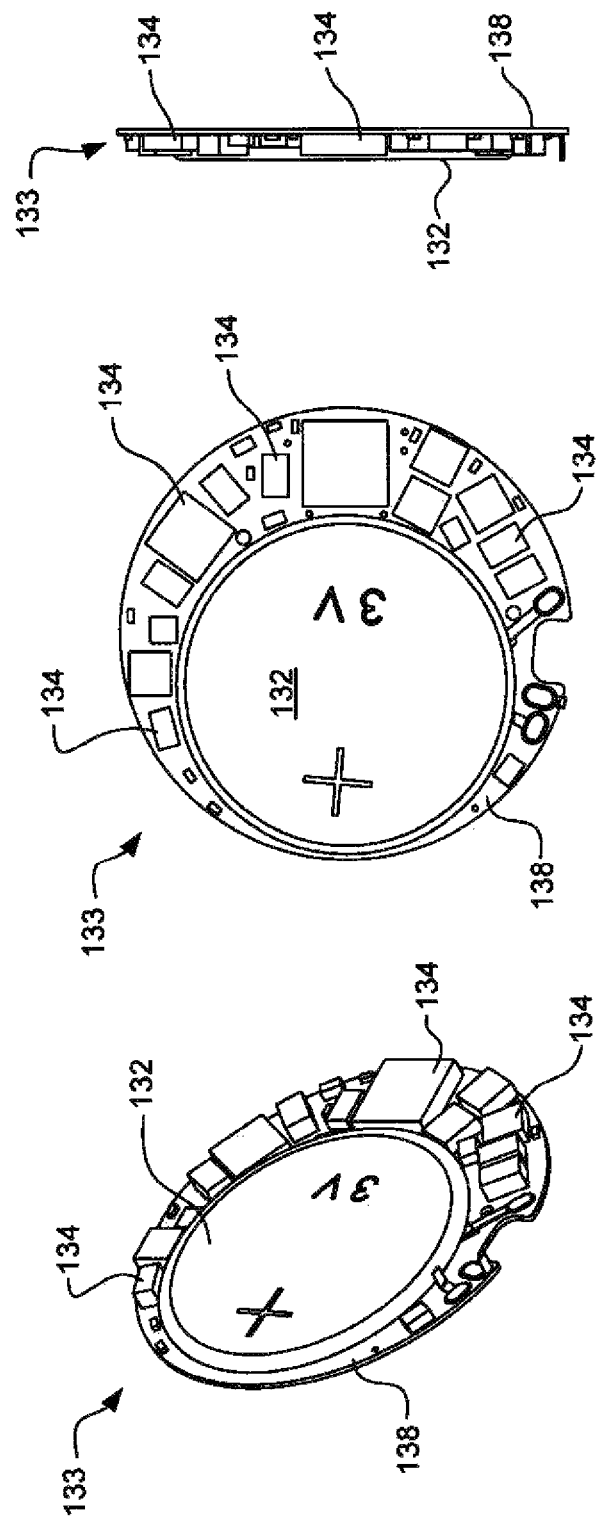

IMPLANTABLE ELECTROACUPUNCTURE DEVICE AND METHOD FOR TREATING CARDIOVASCULAR DISEASE

RELATED APPLICATIONS

This application claims the benefit of the following previously-filed provisional patent applications:
1. VT11-002-01, Implantable Electroacupuncture Device and Method for Treating Cardiovascular Disease, filed Sep. 23, 2011, Appl. No. 61/626,339;
2. VT12-002-01, Electrode Configuration For Implantable Electroacupuncture Device, filed Mar. 6, 2012, Appl. No. 61/606,995;
3. VT12-003-01. Boost Converter Output Control For Implantable Electroacupuncture Device, filed Mar. 12, 2012, Appl. No. 61/609,875;
4. VT12-003-02, Boost Converter Circuit Surge Control For Implantable Electroacupuncture Device Using Digital Pulsed Shutdown, filed Jul. 16, 2012, Appl. No. 61/672,257;
5. VT12-004-01, Smooth Ramp-Up Stimulus Amplitude Control For Implantable Electroacupuncture Device, filed Jul. 17, 2012, Appl. No. 61/672,661;
6. VT12-006-01, Pulse Charge Delivery Control In An Implantable Electroacupuncture Device, filed Jul. 23, 2012, Appl. No. 61/674,691;
7. VT12-008-01, Radial Feed-Through Packaging For An Implantable Electroacupuncture Device, filed Jul. 26, 2012, Appl. No. 61/676,275.

BACKGROUND

Cardiovascular disease, also sometimes referred to as heart disease, cardiac disease or cardiopathy, is an umbrella term for a variety of diseases affecting the heart. Cardiovascular disease includes any of a number of specific diseases that affect the heart itself and/or the blood vessel system, especially the veins and arteries leading to and from the heart. Cardiovascular disease represents one of the more prevalent diseases affecting middle-aged and older aged individuals in both Western and Eastern societies. As of 2007, cardiovascular disease was the leading cause of death in the United States, England, Canada and Wales, accounting for 25.4% of the total deaths in the United States.

In the United States, the most common type of cardiovascular disease is coronary artery disease (CAD). Coronary artery disease is a disease of the artery caused by the accumulation of atheromatous plaques within the walls of the arteries that supply the myocardium (the heart muscle). Angina pectoris (chest pain) and myocardial infarction (heart attack) are symptoms of and conditions caused by coronary artery disease. Heart failure may develop after other conditions have damaged or weakened the heart. CAD is the most common cause of heart failure.

Another type of cardiovascular disease is ischemic heart disease. Ischemia is defined as the inadequate flow of blood to a part of the body caused by constriction or blockage of the blood vessels supplying it. Ischemia of the heart muscle produces angina pectoris. Angina pectoris may be classified as either stable angina pectoris or unstable angina pectoris. Stable angina pectoris is angina pectoris induced by exercise and relieved by rest. Stable angina pectoris occurs when the demand for blood by the heart exceeds the supply of the blood provided by the coronary arteries.

Unstable angina pectoris, also known as "crescendo angina," is a form of acute coronary syndrome. It is defined as angina pectoris that changes or worsens. It occurs unpredictably at rest and may be a serious indicator of an impending heart attack. What differentiates stable angina from unstable angina (other than symptoms) is the pathophysiology of the atherosclerosis. The pathophysiology of unstable angina is the reduction of coronary flow due to transient platelet aggregation. In stable angina, the developing atheroma is protected with a fibrous cap. This cap (atherosclerotic plaque) may rupture in unstable angina, allowing blood clots to precipitate and further decrease the lumen of the coronary vessel. This explains why an unstable angina appears to be independent of activity.

There are currently a wide variety of methods that can be used to treat patients with cardiovascular diseases. These include risk factor reduction (e.g., diet, exercise, stress reduction), pharmacologic therapy (drugs), and invasive and interventional therapies as practiced by cardiologists and surgeons (e.g., bypass surgery).

Despite all the therapeutic measures available and practiced today, many patients remain severely incapacitated by their cardiovascular disease. Thus, in recent years there has been both a profound interest and acceptance of a number of alternative therapies. These therapies have emerged because none of the more usual therapies have been completely effective in eliminating either the symptoms or the adverse outcomes resulting from these diseases. Further, many mainstay therapies are associated with side effects that surprising numbers of patients find unacceptable. Therefore, there has been a surge of interest in alternative therapies. See, e.g., J. C. Longhurst "Central and Peripheral Neural Mechanisms of Acupuncture in Myocardial Ischemia", *International Congress Series* 1238 (2002) 79-87 (hereafter "Longhurst (2002)"); C. Mannheimer et al., "The Problem of Chronic Refractory Angina," *Europoean Heart Journal* (2002) 23, 355-370 (hereafter "Mannheimer (2002)"); J. E. Sanderson, "Electrical Neurostimulators for Pain Relief in Angina," *British Heart Journal* (1990) 63:141-143 (hereafter "Sanderson (1990)").

The alternative approaches that have emerged in the medical management of cardiovascular disease include neuromodulation techniques; e.g., transcutaneous electric nerve stimulation (TENS) and spinal cord stimulation (SCS). Mannheimer (2002) at 360-362.

Neuromodulation techniques, including both TENS and SCS, appear to be safe and generally effective methods of treating angina pectoris. Transcutaneous electric nerve stimulation (TENS) is a neuromodulation technique that is comparable to needle acupuncture. However, instead of needles, standard electrodes are applied over the painful area of the chest wall. The device can usually be used by the patient at home after instruction. When an angina attack occurs or is anticipated, the patient applies stimulation for one to three minutes. It is essential to place the electrodes so that the stimulation paresthesias cover the area of angina pain, as this is the only way to ensure that the proper spinal segment is activated; i.e., the segment that supplies the heart with nerves. Id at 361.

Disadvantageously, skin irritation develops in a large number of patients, making it difficult to continue with this form of TENS therapy. Thus, if long term neuromodulation treatment is needed, as in angina, spinal cord stimulation (SCS) is typically used as a preferable treatment modality. Clinical observations also suggest that spinal cord stimulation may be more effective than TENS. Thus, TENS has recently been used more as a test method for planned implantation, to determine whether myocardial ischemia is really the cause of the patient's pain and to evaluate whether the patient shows good enough compliance to handle a spinal cord stimulator. Id.

Spinal cord stimulation requires implantation surgery. Implantation of the spinal cord system is performed under local anesthesia. The electrode is positioned epidurally so that paresthesia is produced in the region of angina pain radiation. The patient carries an implantable pulse generator in a subcutaneous pouch, typically below the left costal arch (rib cage). The electrode is then connected to the pulse generator by tunneling a subcutaneous lead from the epidural space (adjacent the spine on the back side of the patient) to the subcutaneous pouch below the patient's rib cage (on the front side of the patient). The system is similar to a pacemaker with the electrode placed in the epidural space instead of the heart. Id.

The TENS and SCS methods described above are potent and are capable of, at least temporarily (in the case of TENS), treating myocardial ischemia, such as angina pectoris. However, the use of TENS provides only temporary relief, and use of an SCS system is highly invasive and has potentially debilitating side effects. To use an SCS device to treat angina pectoris requires that a lead must be tunneled all the way from the back side of the patient to the front side of the patient. Such a method is as invasive as, and suffers from most of the same problems as, any major surgery. In addition, the complications associated with epidural placement, tunneling and removal of leads, which include injury, infection, breakage, as well as the need to perform additional surgery, are not trivial.

Another alternative approach for treating cardiovascular disease, and a host of other physiological conditions, illnesses and deficiencies, is acupuncture, which includes traditional acupuncture, acupressure. Acupuncture has been practiced in Eastern civilizations (principally China, but also other Asian countries) for at least 2500 years. It is still practiced today throughout many parts of the world, including the United States and Europe. A good summary of the history of acupuncture, and its potential applications may be found in Cheung, et al., "*The Mechanism of Acupuncture Therapy and Clinical Case Studies*", (Taylor & Francis, publisher) (2001) ISBN 0-415-27254-8, hereafter referred to as "Cheung, *Mechanism of Acupuncture,* 2001." The Forward, as well as Chapters 1-3, 5, 7, 8, 12 and 13 of Cheung, *Mechanism of Acupuncture,* 2001, are incorporated herein by reference.

Despite the practice in Eastern countries for over 2500 years, it was not until President Richard Nixon visited China (in 1972) that acupuncture began to be accepted in Western countries, such as the United States and Europe. One of the reporters who accompanied Nixon during his visit to China, James Reston, from the New York Times, received acupuncture in China for post-operative pain after undergoing an emergency appendectomy under standard anesthesia. Reston experienced pain relief from the acupuncture and wrote about it in The New York Times. In 1973 the American Internal Revenue Service allowed acupuncture to be deducted as a medical expense. Following Nixon's visit to China, and as immigrants began flowing from China to Western countries, the demand for acupuncture increased steadily. Today, acupuncture therapy is viewed by many as a viable alternative form of medical treatment, alongside Western therapies. Moreover, acupuncture treatment is now covered, at least in part, by most insurance carriers. Further, payment for acupuncture services consumes a not insignificant portion of healthcare expenditures in the U.S. and Europe. See, generally, Cheung, *Mechanism of Acupuncture,* 2001, vii.

Acupuncture is an alternative medicine that treats patients by insertion and manipulation of needles in the body at selected points. Novak, Patricia D. et al (1995). *Dorland's Pocket Medical Dictionary* (25th ed.). Philadelphia: (W.B. Saunders Publisher). ISBN 0-7216-5738-9. The locations where the acupuncture needles are inserted are referred to herein as "acupuncture points" or simply just "acupoints". The location of acupoints in the human body has been developed over thousands of years of acupuncture practice, and maps showing the location of acupoints in the human body are readily available in acupuncture books or online. For example, see, "Acupuncture Points Map," found online at: http://www.acupuncturehealing.org/acupuncture-points-map.html. Acupoints are typically identified by various letter/number combinations, e.g., L6, S37. The maps that show the location of the acupoints may also identify what condition, illness or deficiency the particular acupoint affects when manipulation of needles inserted at the acupoint is undertaken.

References to the acupoints in the literature are not always consistent with respect to the format of the letter/number combination. Some acupoints are identified by a name only, e.g., Tongli. The same acupoint may be identified by others by the name followed with a letter/number combination placed in parenthesis, e.g., Tongli (HT5). Alternatively, the acupoint may be identified by its letter/number combination followed by its name, e.g., HT5 (Tongli). The first letter typically refers to a body organ, or other tissue location associated with, or affected by, that acupoint. However, usually only the letter is used in referring to the acupoint, but not always. Thus, for example, the acupoint P-6 is the same as acupoint Pericardium 6 which is the same as PC-6 which is the same as Pe 6 which is the same as Neiguan. For purposes of this patent application, unless specifically stated otherwise, all references to acupoints that use the same name, or the same first letter and the same number, and regardless of slight differences in second letters and formatting, are intended to refer to the same acupoint. Thus, for example, the acupoint Neiguan is the same acupoint as Neiguan (P6), which is the same acupoint as Neiguan (PC6), which is the same acupoint as PC6 (Neiguan), which is the same acupoint as Neiguan (PC-6), which is the same acupoint as Neiguan (Pe-6), which is the same acupoint as P6, P 6, PC6 or PC-6 or Pe 6.

An excellent reference book that identifies all of the traditional acupoints within the human body is *WHO STANDARD ACUPUNCTURE POINT LOCATIONS IN THE WESTERN PACIFIC REGION*, published by the World Health Organization (WHO), Western Pacific Region, 2008 (updated and reprinted 2009), ISBN 978 92 9061 248 7 (hereafter "*WHO Standard Acupuncture Point Locations* 2008"). The Table of Contents, Forward (page v-vi) and General Guidelines for Acupuncture Point Locations (pages 1-21), as well as pages 151 and 154 (which pages illustrate with particularity the location of acupoint PC6) of the *WHO Standard Acupuncture Point Locations* 2008 are included herewith as Appendix D.

While many in the scientific and medical community are highly critical of the historical roots upon which acupuncture has developed, (e.g., claiming that the existence of meridians, qi, yin and yang, and the like have no scientific basis), see, e.g., http://en.wikipedia.org/wiki/Acupuncture, few can refute the vast amount of successful clinical and other data, accumulated over centuries of acupuncture practice, that shows needle manipulation applied at certain acupoints is quite effective.

The World Health Organization and the United States' National Institutes of Health (NIH) have stated that acupuncture can be effective in the treatment of neurological conditions and pain. Reports from the USA's National Center for Complementary and Alternative Medicine (NCCAM), the American Medical Association (AMA) and various USA government reports have studied and commented on the efficacy of acupuncture. There is general agreement that acupuncture is safe when administered by well-trained practitioners using sterile needles, but not on its efficacy as a medical procedure.

An early critic of acupuncture, Felix Mann, who was the author of the first comprehensive English language acupuncture textbook *Acupuncture: The Ancient Chinese Art of Healing*, stated that "The traditional acupuncture points are no more real than the black spots a drunkard sees in front of his eyes." Mann compared the meridians to the meridians of longitude used in geography—an imaginary human construct. Mann, Felix (2000). *Reinventing acupuncture: a new concept of ancient medicine*. Oxford: Butterworth-Heinemann. pp. 14; 31. ISBN 0-7506-4857-0. Mann attempted to combine his medical knowledge with that of Chinese theory. In spite of his protestations about the theory, however, he apparently believed there must be something to it, because he was fascinated by it and trained many people in the West with the parts of it he borrowed. He also wrote many books on this subject. His legacy is that there is now a college in London and a system of needling that is known as "Medical Acupuncture". Today this college trains doctors and Western medical professionals only.

For purposes of this patent application, the arguments for and against acupuncture are interesting, but not that relevant. What is important is that a body of literature exists that identifies several acupoints within the human body that, rightly or wrongly, have been identified as having an influence on, or are otherwise somehow related to, the treatment of various physiological conditions, deficiencies or illnesses, including pain and other conditions associated with myocardial ischemia, such as angina pectoris. With respect to these acupoints, the facts speak for themselves. Either these points do or do not affect the conditions, deficiencies or illnesses with which they have been linked. The problem lies in trying to ascertain what is fact from what is fiction. This problem is made more difficult when conducting research on this topic because the insertion of needles, and the manipulation of the needles once inserted, is more of an art than a science, and results from such research become highly subjective. What is needed is a much more regimented approach for doing acupuncture research.

It should also be noted that other medical research, not associated with acupuncture research, has over the years identified nerves and other locations throughout a patient's body where the application of electrical stimulation produces a beneficial effect for the patient. Indeed, the entire field of neurostimulation deals with identifying locations in the body where electrical stimulation can be applied in order to provide a therapeutic effect for a patient. For purposes of this patent application, such known locations within the body are treated essentially the same as acupoints—they provide a "target" location where electrical stimulation may be applied to achieve a beneficial result, whether that beneficial result is to reduce pain, to treat myocardial ischemia, to treat hypertension, to mitigate some other form of cardiovascular disease or to address some other issue associated with a disease or condition of the patient.

Returning to the discussion regarding acupuncture, some have proposed applying moderate electrical stimulation at selected acupuncture points through needles that have been inserted at those points. See, e.g., http://en.wikipedia.org/wiki/Electroacupuncture. Such electrical stimulation is known as electroacupuncture (EA). According to Acupuncture Today, a trade journal for acupuncturists: "Electroacupuncture is quite similar to traditional acupuncture in that the same points are stimulated during treatment. As with traditional acupuncture, needles are inserted on specific points along the body. The needles are then attached to a device that generates continuous electric pulses using small clips. These devices are used to adjust the frequency and intensity of the impulse being delivered, depending on the condition being treated. Electroacupuncture uses two needles at a time so that the impulses can pass from one needle to the other. Several pairs of needles can be stimulated simultaneously, usually for no more than 30 minutes at a time." "Acupuncture Today: Electroacupuncture". 2004-02-01 (retrieved on-line 2006-08-09 at http://www.acupuncturetoday.com/abc/electroacupuncture.php).

Recent research has reported the use of electroacupuncture (EA) for the treatment of myocardial ischemia and pain relief in angina. See, e.g., J. Gao, et al., "Acupuncture pretreatment protects heart from injury in rats with myocardial ischemia and reperfusion via inhibition of the $\beta_1$-adrenoceptor signaling pathway," Life Sciences 80 (2007) 1484-1489 (hereafter "Gao (2007)"); Longhurst (2002); P. Li et al., "Reversal of Reflex-Induced Myocardial Ischemia by Median Nerve Stimulation: A Feline Model of Electroacupuncture," American Heart Association Circulation 1998, 97:1186-1194 (hereafter "Li (1998)"); Sanderson (1990).

The reason why acupuncture, including EA, can be used to treat angina is discussed at length in Cheung, *Mechanism of Acupuncture*, 2001, chapter 8, previously incorporated herein by reference.

Similar techniques for using electrical devices, including external EA devices, for stimulating peripheral nerves and other body locations for treatment of various maladies are known in the art. See, e.g., U.S. Pat. Nos. 4,535,784; 4,566,064; 5,195,517; 5,250,068; 5,251,637; 5,891,181; 6,393,324; 6,006,134; 7,171,266; and 7,171,266. The methods and devices disclosed in these patents, however, typically utilize either large implantable stimulators having long leads that must be tunneled through tissue to reach the desired stimulation site, or use external devices that must interface with implanted electrodes via percutaneous leads or wires passing through the skin. Such devices and methods are still far too invasive, or are ineffective, and thus are subject to the same limitations and concerns, as are the previously described electrical stimulation devices.

From the above, it is seen that there is a need in the art for a less invasive device and technique for electroacupuncture stimulation of acupoints that does not require the continual use of needles inserted through the skin, or long insulated wires implanted or inserted into blood vessels, for the purposes of treating cardiovascular diseases.

SUMMARY

One characterization of the invention described herein is an Implantable ElectroAcupuncture Device (IEAD) that treats cardiovascular disease through the application of electroacupuncture (EA) stimulation pulses at acupoint PC6 in the left or right forearm of a patient. The IEAD includes: (1) a small IEAD housing having an electrode configuration thereon that includes at least two electrodes, (2) pulse generation circuitry located within the IEAD housing that delivers EA stimulation pulses to the patient's body tissue at acupoint PC6, (3) a primary battery also located within the IEAD housing that provides the operating power for the IEAD to perform its intended function, and (4) a sensor located within the IEAD housing that is responsive to operating commands wirelessly communicated to the IEAD from a non-implanted location, these operating commands allowing limited external control of the IEAD, such as ON/OFF and EA stimulation pulse amplitude adjustment.

In one preferred embodiment, the IEAD housing used as part of the invention is coin-sized and -shaped, having a nominal diameter of 23 mm, and a thickness of only 2 to 3 mm.

One preferred embodiment provides a symmetrical electrode configuration on the housing of the IEAD. Such symmetrical electrode configuration includes at least two electrodes, at least one of which is located substantially in the center of a first surface of the IEAD housing, and is referred to as a central electrode. The other electrode is symmetrically positioned around and at least 5 mm distant from the center of the central electrode, and is referred to as an annular or ring electrode (or, in some instances, as a circumscribing electrode). This symmetry between the central electrode and the annular electrode advantageously focuses the electric field, and hence the EA stimulation current created by application of an EA stimulation pulse to the electrodes, deep into the tissue below the central electrode, where the desired EA stimulation at acupoint PC6 occurs. Hence, when implanted, the first surface of the IEAD housing is faced inwardly into the patient's tissue below acupoint PC6, and a second surface of the IEAD housing, on the opposite side of the housing from the first surface, is faced outwardly to the patient's skin. One preferred embodiment of the IEAD housing uses one centrally located cathode electrode on the first surface of the IEAD housing, and one ring anode electrode located on a perimeter edge of a coin-sized and -shaped IEAD housing.

The pulse generation circuitry located within the IEAD housing is coupled to the at least two electrodes. This pulse generation circuitry is configured to generate EA stimulation pulses in accordance with a specified stimulation regimen. This stimulation regimen defines the duration and rate at which a stimulation session is applied to the patient. The stimulation regimen requires that the stimulation session have a duration of no more than T3 minutes and a rate of occurrence of no more than once every T4 minutes. Advantageously, the duty cycle of the stimulation sessions, i.e., the ratio of T3/T4, is very low, no greater than 0.05. A representative value for T3 is 30 minutes, and a representative value for T4 is 7 days. The individual EA stimulation pulses that occur within the stimulation session also have a duty cycle measured relative to the period (the inverse of the frequency or rate of the stimulation pulses) of no greater than 1%. A representative pulse width and frequency for the EA stimulation pulses is 0.1 milliseconds, occurring at a pulse rate of 2 Hz.

The primary battery contained within the IEAD housing and electrically coupled to the pulse generation circuitry has a nominal output voltage of 3 volts, and an internal battery impedance that is at least 5 ohms, and may be as high as 150 ohms or more. Advantageously, electronic circuitry within the IEAD housing controls the value of the instantaneous surge current that may be drawn from the battery in order to prevent any large drops in the battery output voltage. Avoiding large drops in the battery output voltage assures that the circuits within the IEAD will continue to operate as designed without failure. Being able to use a primary battery that has a relatively high internal impedance allows the battery to be thinner, and thus allows the device to be thinner and more easily implanted. The higher internal impedance also opens the door to using relatively inexpensive commercially-available disc batteries as the primary battery within the IEAD, thereby greatly enhancing the manufacturability of the IEAD and significantly lowering its cost.

Another characterization of the invention described herein may be described as a first method of treating cardiovascular disease in a patient using a leadless, coin-sized implantable electroacupuncture device (IEAD). Such IEAD is powered by a small disc battery having a specified nominal output voltage of about 3.0 volts, and having an internal impedance of at least 5 ohms.

The IEAD used to practice this first method is configured, using electronic circuitry within the IEAD, to generate EA stimulation pulses in accordance with a specified stimulation regimen. The EA stimulation pulses generated in accordance with this stimulation regimen are applied to the patient's tissue through at least two electrodes located on the housing of the IEAD. These two electrodes include at least one central electrode, located in the center of a bottom surface of the IEAD housing, and at least one annular electrode that surrounds the central electrode. The edge of the annular electrode closest to the central electrode is separated from the center of the central electrode by at least 5 mm.

Using such an IEAD, the cardiovascular disease treatment provided by this first method includes the steps of: (a) implanting the IEAD below the skin surface of the patient at acupoint PC-6 in the left and/or right forearm with its bottom surface (the "bottom" surface of the IEAD is that surface on which the central electrode is placed) facing into the patient's tissue below the patient's skin surface at acupoint PC6; and (b) enabling the IEAD to provide stimulation pulses in accordance with a specified stimulation regimen.

The stimulation regimen, when enabled, provides a stimulation session at a rate of once every T4 minutes, with each stimulation session having a duration of T3 minutes. The ratio of T3/T4 is no greater than 0.05. A preferred stimulation session time T3 is 30 minutes, but T3 could be as short as 10 minutes or as long as 60 minutes. A preferred time between stimulation sessions T4 is 7 days, but it could be as short as ½ day or as long as 14 days, or longer, as needed to suit the needs of a particular patient.

Still further, the invention described herein may be characterized as a second method for treating cardiovascular disease in a patient. This second method comprises the steps of: (a) implanting a coin-sized electroacupuncture (EA) device in the patient just below the patient's skin at acupoint PC6; (b) enabling the EA device to generate EA stimulation sessions at a duty cycle that is less than 0.05, wherein each stimulation session comprises a series of EA stimulation pulses; and (c) delivering the EA stimulation pulses of each stimulation session to the specified acupoint through at least two electrodes attached to an outside surface of the EA device. The duty cycle of the stimulation sessions is the ratio of T3/T4, where T3 is the duration in minutes of each stimulation session, and T4 is the time in minutes between stimulation sessions.

In a preferred application for this second method, the electrodes attached to the outside surface of the EA device are arranged in a symmetrical pattern. This symmetrical pattern of electrodes advantageously concentrates, or focuses, the electric field emanating from the electrode(s) downward into the tissue below the selected acupoint to a location where the electroacupuncture stimulation is most effective. Another preferred application is for the electrodes to be aligned along the axis of two or more acupoints, e.g., PC6 and PC5.

Additionally, the invention described herein may be characterized as a method of assembling an implantable electroacupuncture device (IEAD) for use in treating cardiovascular disease (e.g., heart failure, coronary artery disease, myocardial ischemia or angina). The IEAD is assembled so as to reside in a round, thin, hermetically-sealed, coin-sized housing. An important feature of the coin-size housing, and the method of assembly associated therewith, is that it electrically and thermally isolates a feed-through pin assembly radially passing through a wall of the coin-sized housing from the high temperatures associated with welding the housing closed to hermetically seal its contents. Such method of assembling includes the steps of:

a. forming a coin-sized housing having a bottom case and a top cover plate, the top cover plate being adapted to fit over the bottom case, the bottom case being substantially round and having a diameter D2 that is nominally 23 mm and a perimeter side wall extending all the way around the perimeter of the bottom case, the perimeter side wall having a height W2, wherein the ratio of W2 to D2 is no greater than about 0.13;

b. forming a recess in one segment of the side wall, the recess extending radially inwardly from the side wall to a depth D3, and the recess having an opening in a bottom wall portion thereof;

c. hermetically sealing a feed-through assembly in the opening in the bottom of the recess, the feed-through assembly having a feed-through pin that passes through the opening without contacting the edges of the opening, a distal end of the pin extending radially outward beyond the side wall of the bottom case, and a proximal end of the feed-through pin extending radially inward toward the center of the bottom case, whereby the feed-through pin assembly is hermetically bonded to the opening in the side wall at a location in the bottom of the recess that is a distance D3 from the perimeter side wall, thereby thermally isolating the feed-through assembly from the high temperatures that occur at the perimeter side wall when the cover plate is welded to the edge of the perimeter side wall;

d. attaching a central electrode to the thin, coin-sized housing at a central location on the bottom outside surface of the feed-through housing;

e. inserting an electronic circuit assembly, including a battery, inside of the bottom case, and connecting the proximal end of the feed-though pin to an output terminal of the electronic circuit assembly, and electrically connecting the bottom case to a reference terminal of the battery;

f. baking out the assembly to remove moisture, back filling with a mixture of He/Ar inert gas, and then welding the top cover plate to the edges of the side wall of the bottom case, thereby hermetically sealing the electronic circuit assembly, including the battery, inside of the thin, coin-sized IEAD housing;

g. leak testing the welded assembly to assure a desired level of hermeticity has been achieved;

h. placing an insulating layer of non-conductive material around the perimeter edge of the thin coin-sized housing, then placing a circumscribing electrode over the insulating layer of non-conductive material, and then electrically connecting the distal end of the feed-through pin to the circumscribing electrode; and i. covering all external surface areas of the thin, coin-sized housing with a layer of non-conductive material except for the circumscribing electrode around the perimeter of the coin-sized housing and the central electrode centrally located on the bottom surface of the thin-coin-sized housing.

BRIEF DESCRIPTION OF THE DRAWINGS

The above and other aspects, features and advantages of the invention will be more apparent from the following more particular description thereof, presented in conjunction with the following drawings. These drawings illustrate various embodiments of the principles described herein and are part of the specification. The illustrated embodiments are merely examples and do not limit the scope of the disclosure.

FIG. 2 shows a plan view of the bottom surface of the IEAD housing illustrated in FIG. 1.

FIG. 2A shows a side view of the IEAD housing illustrated in FIG. 1.

FIG. 3 shows a plan view of one side, indicated as the "skin" side, of the IEAD housing or case illustrated in FIG. 1.

FIG. 3A is a sectional view of the IEAD of FIG. 3 taken along the line A-A of FIG. 3.

FIG. 5 is a plan view of the empty IEAD housing shown in FIG. 4.

FIG. 5A depicts a sectional view of the IEAD housing of FIG. 5 taken along the section line A-A of FIG. 5.

FIG. 5B shows an enlarged view or detail of the portion of FIG. 5A that is encircled with the line B.

FIG. 6 is a perspective view of an electronic assembly, including a battery, that is adapted to fit inside of the empty housing of FIG. 4 and FIG. 5.

FIGS. 6A and 6B show a plan view and side view, respectively, of the electronic assembly shown in FIG. 6.

Figure 1:
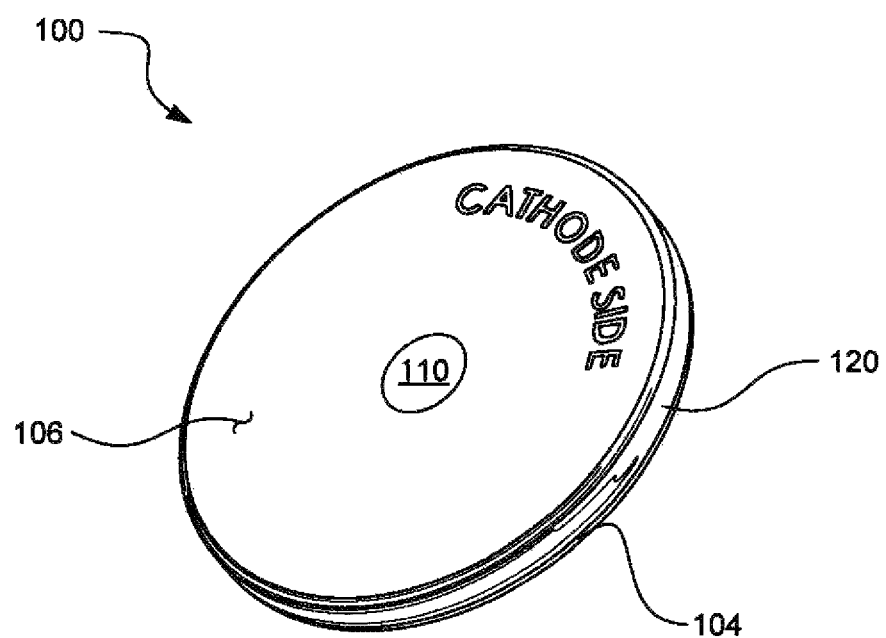
FIG. 1 is a perspective view of an Implantable Electroacupuncture Device (IEAD) made in accordance with the teachings presented herein.

Appendix A, submitted herewith, illustrates some examples of alternate symmetrical electrode configurations that may be used with an IEAD of the type described herein.

Appendix B, submitted herewith, illustrates a few examples of non-symmetrical electrode configurations that may be used with an IEAD made in accordance with the teachings herein.

Appendix C, submitted herewith, shows an example of the code used in the micro-controller IC (e.g., U2 in FIG. 14) to control the basic operation and programming of the IEAD, e.g., to Turn the IEAD ON/OFF, adjust the amplitude of the stimulus pulse, and the like, using only an external magnet as an external communication element.

Appendix D, submitted herewith, contains selected pages from the *WHO Standard Acupuncture Point Locations* 2008 reference book, referred to in paragraph [0017].

Appendices A, B, C and D are incorporated by reference herein, and comprise a part of the specification of this patent application.

Throughout the drawings and appendices, identical reference numbers designate similar, but not necessarily identical, elements.

DETAILED DESCRIPTION

Overview

Disclosed and claimed herein is an implantable, coin-shaped, self-contained, leadless electroacupuncture (EA) device having at least two electrode contacts mounted on the surface of its housing. In one preferred embodiment, the electrodes include a central cathode electrode on a bottom side of the housing, and an annular anode electrode that surrounds the cathode. In another preferred embodiment, the anode annular electrode is a ring electrode placed around the perimeter edge of the coin-shaped housing.

The EA device is leadless. This means there are no leads or electrodes at the distal end of leads (common with most implantable electrical stimulators) that have to be positioned and anchored at a desired stimulation site. Also, because there are no leads, no tunneling through body tissue or blood vessels is required in order to provide a path for the leads to return and be connected to a tissue stimulator (also common with most electrical stimulators).

The EA device is adapted to be implanted through a very small incision, e.g., less than 2-3 cm in length, directly adjacent to a selected acupuncture site ("acupoint") known to moderate or affect a hypertension condition of a patient.

The EA device is easy to implant. Also, most embodiments are symmetrical. This means that there is no way that it can be implanted incorrectly (unless the physician puts it in up-side-down, which would be difficult to do given the markings on its case). All that need be done is to cut the incision, and slide the device in place through the incision. Once the implant pocket has been prepared, it is as easy as sliding a coin into a slot. Such implantation can usually be completed in less than 10 minutes in an outpatient setting, or in a doctor's office. Only minor, local anesthesia need be used. No major or significant complications are envisioned for the implant procedure. The EA device can also be easily and quickly explanted, if needed.

The EA device is self-contained. It includes a primary battery to provide its operating power. It includes all of the circuitry it needs, in addition to the battery, to allow it to perform its intended function for several years. Once implanted, the patient will not even know it is there, except for a slight tingling that may be felt when the device is delivering stimulus pulses during a stimulation session. Also, once implanted, the patient can just forget about it. There are no complicated user instructions that must be followed. Just turn it on. No maintenance is needed. Moreover, should the patient want to disable the EA device, i.e., turn it OFF, or change stimulus intensity, he or she can do so using, e.g., an external magnet.

The EA device can operate for several years because it is designed to be very efficient. Stimulation pulses applied by the EA device at a selected acupoint through its electrodes formed on its case are applied at a very low duty cycle in accordance with a specified stimulation regimen. The stimulation regimen applies EA stimulation during a stimulation session that lasts at least 10 minutes, typically 30 minutes, and rarely longer than 60 minutes. These stimulation sessions, however, occur at a very low duty cycle. In one preferred treatment regimen, for example, a stimulation session having a duration of 30 minutes is applied to the patient just once a week. The stimulation regimen, and the selected acupoint at which the stimulation is applied, are designed and selected to provide efficient and effective EA stimulation for the treatment of the patient's hypertension condition.

The EA device is, compared to most implantable medical devices, relatively easy to manufacture and uses few components. This not only enhances the reliability of the device, but helps keep the manufacturing costs low, which in turn allows the device to be more affordable to the patient. One key feature included in the mechanical design of the EA device is the use of a radial feed-through assembly to connect the electrical circuitry inside of its housing to one of the electrodes on the outside of the housing. The design of this radial feed-through pin assembly greatly simplifies the manufacturing process. The process places the temperature sensitive hermetic bonds used in the assembly—the bond between a pin and an insulator and the bond between the insulator and the case wall—away from the perimeter of the housing as the housing is hermetically sealed at the perimeter with a high temperature laser welding process, thus preserving the integrity of the hermetic bonds that are part of the feed-through assembly.

In operation, the EA device is safe to use. There are no horrific failure modes that could occur. Because it operates at a very low duty cycle (i.e., it is OFF much, much more than it is ON), it generates little heat. Even when ON, the amount of heat it generates is not much, less than 1 mW, and is readily dissipated. Should a component or circuit inside of the EA device fail, the device will simply stop working. If needed, the EA device can then be easily explanted.

Another key feature included in the design of the EA device is the use of a commercially-available battery as its primary power source. Small, thin, disc-shaped batteries, also known as "coin cells," are quite common and readily available for use with most modern electronic devices. Such batteries come in many sizes, and use various configurations and materials.

However, insofar as inventors or applicant are aware, such batteries have never been used in implantable medical devices previously. This is because their internal impedance is, or has always thought to have been, much too high for such batteries to be of practical use within an implantable medical device where power consumption must be carefully monitored and managed so that the device's battery will last as long as possible, and so that dips in the battery output voltage (caused by any sudden surge in instantaneous battery current) do not occur that could compromise the performance of the device. Furthermore, the energy requirements of other active implantable therapies are far greater than can be provided by such coin cells without frequent replacement.

The EA device disclosed herein advantageously employs power-monitoring and power-managing circuits that prevent any sudden surges in battery instantaneous current, or the resulting drops in battery output voltage, from ever occurring, thereby allowing a whole family of commercially-available, very thin, high-output-impedance, relatively low capacity, small disc batteries (or "coin cells") to be used as the EA device's primary battery without compromising the EA device's performance. As a result, instead of specifying that the EA device's battery must have a high capacity, e.g., greater than 200 mAh, with an internal impedance of, e.g., less than 5 ohms, which would either require a thicker battery and/or preclude the use of commercially-available coin-cell batteries, the EA device of the present invention can readily employ a battery having a relatively low capacity, e.g., less than 60 mAh, and a high battery impedance, e.g., greater than 5 ohms.

Moreover, the power-monitoring, power-managing, as well as the pulse generation, and control circuits used within the EA device are relatively simple in design, and may be readily fashioned from commercially-available integrated circuits (IC's) or application-specific integrated circuits (ASIC's), supplemented with discrete components, as needed. In other words, the electronic circuits employed within the EA device need not be complex nor expensive, but are simple and inexpensive, thereby making it easier to manufacture the EA device and to provide it to patients at an affordable cost.

DEFINITIONS

As used herein, "annular", "circumferential", "circumscribing", "surrounding" or similar terms used to describe an electrode or electrode array, or electrodes or electrode arrays, (where the phrase "electrode or electrode array," or "electrodes or electrode arrays," is also referred to herein as "electrode/array," or "electrodes/arrays," respectively) refers to an electrode/array shape or configuration that surrounds or encompasses a point or object, such as another electrode, without limiting the shape of the electrode/array or electrodes/arrays to be circular or round. In other words, an "annular" electrode/array (or a "circumferential" electrode/array, or a "circumscribing" electrode/array, or a "surrounding" electrode/array), as used herein, may be many shapes, such as oval, polygonal, starry, wavy, and the like, including round or circular.

"Nominal" or "about" when used with a mechanical dimension, e.g., a nominal diameter of 23 mm, means that there is a tolerance associated with that dimension of no more than plus or minus (+/−) 5%. Thus, a dimension that is nominally 23 mm means a dimension of 23 mm+/−(0.05×23 mm=1.15 mm).

"Nominal" when used to specify a battery voltage is the voltage by which the battery is specified and sold. It is the voltage you expect to get from the battery under typical conditions, and it is based on the battery cell's chemistry. Most fresh batteries will produce a voltage slightly more than their nominal voltage. For example, a new nominal 3 volt lithium coin-sized battery will measure more than 3.0 volts, e.g., up to 3.6 volts under the right conditions. Since temperature affects chemical reactions, a fresh warm battery will have a greater maximum voltage than a cold one. For example, as used herein, a "nominal 3 volt" battery voltage is a voltage that may be as high as 3.6 volts when the battery is brand new, but is typically between 2.7 volts and 3.4 volts, depending upon the load applied to the battery (i.e., how much current is being drawn from the battery) when the measurement is made and how long the battery has been in use.

Conditions Treated

As indicated previously, cardiovascular disease is an umbrella term for a variety of diseases affecting the heart. Cardiovascular disease includes any of a number of specific diseases that affect the heart itself and/or the blood vessel system, especially the veins and arteries leading to and from the heart. For purposes of this patent application, the cardiovascular diseases best treated by the EA device described herein, and the methods of using such EA device, are focused on the following conditions: (1) heart failure; (2) coronary artery disease (also sometimes referred to as coronary heart disease, and abbreviated as "CAD" or "CHD"); (3) myocardial ischemia; and (4) angina. Each of these four conditions is described in more detail in the paragraphs that follow.

The first of the cardiovascular conditions treated by the device and methods described herein is heart failure. Heart failure develops in response to an insult resulting in a decline in the pumping capacity of the heart. (Note, an "insult" in medical terms is a bodily injury, irritation, or other trauma.) In response to the decline in pumping capacity, compensatory neurohumoral mechanisms are activated. Among others, the Sympathetic Nervous System (SNS), the Renin Angiotensin Aldosterone System (RAAS), and the Cytokine System, are activated. Sympathetic nervous system activation has been associated with progression of heart failure, increased sudden death risk, and increased mortality. Initially, these neurohumoral mechanisms are able to compensate for the depressed heart function and maintain hemodynamic stability. However, long-term activation of these neurohumoral mechanisms has deleterious effects on cardiac structure and performance, leading to cardiac decompensation and heart failure progression. Heart failure patients with the greatest sympathetic activation have the worst prognosis. Pharmacologic treatment of heart failure is focused on interruption of this sympathetic activation with stability or improvement in cardiac function and decreased mortality.

The role of increased sympathetic activity in the progression of heart failure is well understood. The most heightened sympathetic activity is positively associated with the worst prognosis in heart failure. Thus, the normalization of sympathetic activity is a target in the treatment of heart failure. International guidelines for the treatment of heart failure and myocardial infarction focus on reducing the severity of the neurohormonal activation. The benefits of beta-blocker therapy, for example, as a pharmaceutical targeting of the inhibition of the SNS, is considered a worthwhile treatment to attenuate the progression of heart failure.

Heart failure means that the heart is unable to pump enough blood to meet the needs of the body. In addition to hypertension, coronary artery disease (CAD)—the narrowing of the arteries in the heart—may lead to heart failure. The narrowed arteries may limit the heart's supply of oxygen rich blood resulting in weakened heart muscles. Most commonly the narrowing is caused by plaque buildup on (or, atherosclerosis of) the coronary arteries. As a result of the narrowing and limited blood supply to the heart (characterized as myocardial ischemia), chest pain called angina often results. A complete blockage can cause a myocardial infarction (a heart attack).

In a small study of 20 patients with advanced heart failure who underwent acute mental stress testing to examine changes in sympathetic activity associated with that stress, those patients who underwent active acupuncture treatment did not have increased sympathetic activity after acupuncture and mental stress testing, unlike the control group who experienced a 25% increase. Middlekauff H R, Yu J L, Hui K, et al.: "Acupuncture inhibits sympathetic activation during mental stress in advanced heart failure patients," *J Cardiac Failure:* 8:399-406 (2002).

Additionally, acupuncture in hypertensive patients and its effect on sympathetic activity is suggestive of utility in heart failure. See, e.g., Longhurst J C: "Acupuncture's beneficial effects on the cardiovascular system," *Prev Cardiol:* 1:21-33 (1998).

The second of the cardiovascular conditions treated by the device and methods described herein is coronary artery disease (also sometimes referred to as coronary heart disease, and abbreviated as "CAD" or "CHD", respectively). The current science in acupuncture suggests that the mechanism of acupuncture therapy for CAD involves improvement in the neurohumoral regulation, the increase of coronary blood flow and myocardial oxygen supply, and the reduction of myocardial oxygen consumption, thereby improving myocardial ischemia.

In a Japanese study, three patients with coronary artery disease who were treated by acupuncture at PC6 had a decrease in angina episodes during workload and an improvement in clinical symptoms. Oka, T., Y. Tsuda, S. Suzuki, R. Aji, S. Kaneya and T. Fujino: "Treatment of angina pectoris with acupuncture—role of 'Neiguan,'" *Jpn. J. Oriental Med.* 38: 85-88 (1987, in Japanese).

In another Japanese study, the measured effect of acupuncture on coronary artery dilatation during coronary angiography was 68% of that produced by isosorbide dinitrate. Kurono Y, Egawa M, Yano T, Shimoo K: "The effect of acupuncture on the coronary arteries as evaluated by coronary angiography: a preliminary report," *Am J Chin Med* 30: 387-396 (2002).

In patients who underwent coronary artery bypass grafting in coronary artery disease, acupuncture applied at HT7 and PC6 increased cardiac output and improved heart function better than in the control group, which used drugs only. Lin D, Lin Y, Hu J, Ruan X: "Effect of Electroacupuncture on Neiguan and Shenmen Points on heart function after coronary artery bypass grafting in coronary heart disease." Modern Journal of Integrated Traditional Chinese and Western Medicine: 18:2241-41. Abstract. (2009).

The third of the cardiovascular conditions treated by the device and methods described herein is myocardial ischemia. In animals, acupuncture has been shown to reduce electrocardiogram (ECG) evidence of myocardial ischemia while improving regional wall motion. See, Li P, Pitsillides K F, Rendig S V et al: "Reversal of reflex-induced myocardial ischemia by median nerve stimulation: a feline model of electroacupuncture," *Circulation* 97: 1186-94 (1998); Longhurst J C: "Central and peripheral neural mechanisms of acupuncture in myocardial ischemia," *Intl Congress Series* 1238:79-87(9) (2002). Various animal studies have shown improvement of experimental myocardial ischemia by the acupuncture or electroacupuncture of PC6 (sometimes alone but more often alongside other acupoints) Liu X Q, Lu S Q, Luo L: "Influence of acupuncture on epicardial monophasic action potential in vivo in dog with myocardial infarction," *Tianjin Journal of Traditional Chinese Medicine* 22: 480-481 (2005).

Additionally, in a randomized controlled trial, electroacupuncture has been shown to alleviate cardiac ischemia-repurfusion injury in adult patients underoing heart valve replacement surgery. Yang L, Yang J, Wang Q, et al.: "Cardioprotective effects of electroacupuncture pretreatment on patients undergoing heart valve replacement surgery: a randomized controlled trial," *Ann Thorac Surg* 89:781-6 (2010). Electroacupuncture was performed bilaterally at acupoints PC6, LU7, and LU2 once a day for 30 minutes over the five days preceding valve surgery. It is unclear what mechanism underlies these positive results; however, it may corroborate other research suggesting reduced oxygen demand.

The fourth of the cardiovascular conditions treated by the device and methods described herein is angina. In one of the first randomized trials to compare the effectiveness of acupuncture and sham acupuncture in patients with severe, stable angina pectoris resistant to medical treatment, Ballegaard et. al showed that the active treatment group had significantly higher difference in pressure-rate-product between rest and maximum exercise (dPRP) and higher maximal pressure-rate-product (PRP), which was interpreted as an increase in cardiac functional capacity. Ballegaard S, Jensen G, Pedersen F et al: "Acupuncture in severe, stable angina pectoris: a randomized trial," Acta Med Scand 220: 307-13 (1986). The investigators suggested that the change was caused by a decreased afterload secondary to systemic vasodilation specific to particular acupoints and not due to other control acupoints at the same spinal cord level. The active acupuncture points were bilateral and manual applied at PC6, ST36, and UB14.

In another study by Richter et al, individualized acupuncture was done on patients with stable angina with success. Richter A, Herlitz J, Hjalmarson A: "Effect of acupuncture in patients with angina pectoris," *Eur Heart J:* 12:175-8 (1991). The maximum workload until onset of chest pain was significantly increased. However, not much difference was observed in exercise capacity in comparison to the placebo therapy at the end of the acupuncture period. Investigators concluded some relief of myocardial ischemia, possibly by influencing coronary perfusion. While the acupuncture was individualized, five main points were used: PC6, HT5, UB15, UB20 and ST36; and, some additional points include HT7, LI4, LI11, and LV3.

With respect to the location where inventors or applicant (hereafter "inventors or applicant" are referred to collectively as "Applicant") have chosen to apply electroacupuncture (EA) stimulation for purposes of the cardiovascular treatment methods described herein, the acupoint PC6 (Neiguan), or a point near PC6, such as a point along an axis line connecting PC6 with a nearby acupoint, such as PC5 or PC7, is preferred. The location of acupoint PC6 is illustrated and described on pages 151 and 154 of *WHO Standard Acupuncture Point Locations* 2008, previously incorporated herein by reference. Selected portions of *WHO Standard Acupuncture Point Locations* 2008, including pages 151 and 154 are included in Appendix D.

Mechanical Design

Turning first to FIG. 1, there is shown a perspective view of one preferred embodiment of an implantable electroacupuncture device (IEAD) made in accordance with the teachings disclosed herein. The IEAD 100 may also sometimes be referred to as an implantable electroacupuncture stimulator (IEAS). As seen in FIG. 1, the preferred IEAD 100 has the appearance of a disc or coin, having a top side 102, a bottom side 106 and an edge side 104.

As used herein, the "top" side of the IEAD 100 is the side that is positioned closest to the skin of the patient when the IEAD is implanted. The "bottom" side is the side of the IEAD that is farthest away from the skin when the IEAD is implanted. The "edge" of the IEAD is the side that connects or joins the top side to the bottom side. In FIG. 1, the IEAD 100 is oriented to show the bottom side 106 and a portion of the edge side 104.

Many of the features associated with the mechanical design of the IEAD 100 shown in FIG. 1 are the subject of a prior U.S. Provisional Patent Application, entitled "Radial Feed-Through Packaging for An Implantable Electroacupuncture Device", Application No. 61/676,275, filed 26 Jul. 2012, which application is incorporated here by reference.

It should be noted here that throughout this application, the terms IEAD 100, IEAD housing 100, bottom case 124, can 124, or IEAD case 124, or similar terms, are used to describe the housing structure of the EA device. In some instances, it may appear these terms are used interchangeably. However, the context should dictate what is meant by these terms. As the drawings illustrate, particularly FIG. 7, there is a bottom case 124 that comprises the "can" or "container" wherein the components of the IEAD 100 are first placed and assembled during manufacture of the IEAD 100. When all of the components are assembled and placed within the bottom case 124, a top plate 122 is welded to the bottom case 124 to form the hermetically-sealed housing of the IEAD. The cathode electrode 110 is attached to the outside of the bottom case 124, and the ring anode electrode 120 is attached, along with its insulating layer 129, around the perimeter edge 104 of the bottom case 124. Finally, a layer of silicone molding 125 covers the IEAD housing except for the outside surfaces of the anode ring electrode and the cathode electrode.

Figure 7:
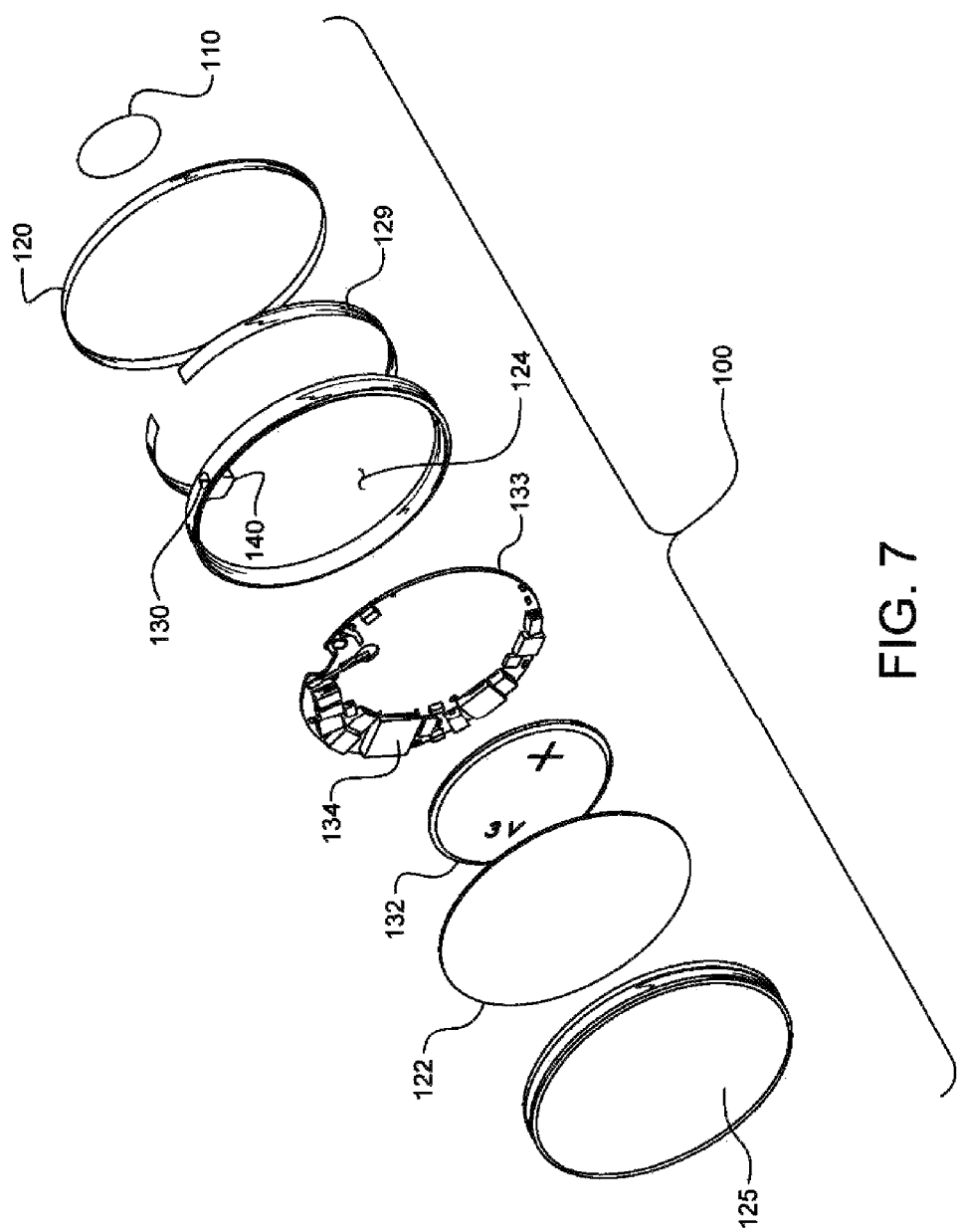
FIG. 7 is an exploded view of the IEAD assembly, illustrating its constituent parts.

The embodiment of the IEAD 100 shown in FIG. 1 utilizes two electrodes, a cathode electrode 110 that is centrally positioned on the bottom side 106 of the IEAD 100, and an anode electrode 120. The anode electrode 120 is a ring electrode that fits around the perimeter edge 104 of the IEAD 100. Not visible in FIG. 1, but which is described hereinafter in connection with the description of FIG. 7, is a layer of insulating material 129 that electrically insulates the anode ring electrode 120 from the perimeter edge 104 of the housing or case 124.

Not visible in FIG. 1, but a key feature of the mechanical design of the IEAD 100, is the manner in which an electrical connection is established between the ring electrode 120 and electronic circuitry carried inside of the IEAD 100. This electrical connection is established using a radial feed-through pin that fits within a recess formed in a segment of the edge of the case 124, as explained more fully below in connection with the description of FIGS. 5, 5A, 5B and 7.

In contrast to the feed-through pin that establishes electrical contact with the anode electrode, electrical connection with the cathode electrode 110 is established simply by forming or attaching the cathode electrode 110 to the bottom 106 of the IEAD case 124. This is because the case 124 is electrically connected to a reference potential of 0 volts, i.e., ground potential, on the inside of the IEAD case 124. In order to prevent the entire case 124 from functioning as the cathode (which is done to better control the electric fields established between the anode and cathode electrodes), the entire IEAD housing is covered in a layer of silicone molding 125 (see FIG. 7), except for the outside surface of the anode ring electrode 120 and the cathode electrode 110.

The advantage of using a central cathode electrode and a ring anode electrode is described in U.S. Provisional Patent Application No. 61/672,257, filed 6 Mar. 2012, entitled "Electrode Configuration for Implantable Electroacupuncture Device", which application is incorporated herein by reference. One significant advantage of this electrode configuration is that it is symmetrical. That is, when implanted, the surgeon or other medical personnel performing the implant procedure, need only assure that the cathode side of the IEAD 100 is facing down, i.e., facing deeper into the tissue, and that the IEAD is over the desired acupoint, or other tissue location, that is intended to receive the electroacupuncture (EA) stimulation. The orientation of the IEAD 100 is otherwise not important.

Figure 1A:
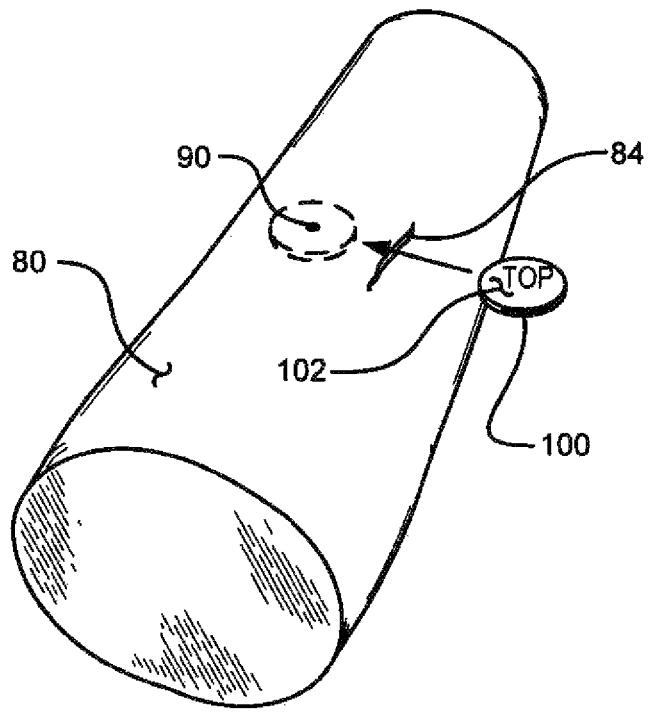
FIG. 1A shows a view of a patient's arm where acupoint PC6 has been identified, and illustrates the manner used to implant an IEAD at the selected acupoint PC6.

Implantation of the IEAD is illustrated in FIG. 1A. Shown in FIG. 1A is a limb 80 of the patient wherein an acupoint 90 has been identified that is to receive acupuncture treatment (in this case electroacupuncture treatment). An incision 82 is made into the limb 80 a short distance, e.g., 10-15 mm, away from the acupoint 90. A slot 84 (parallel to the arm) is formed at the incision by lifting the skin closest to the acupoint up at the incision. As necessary, the surgeon may form a pocket under the skin at the acupoint location. The IEAD 100, with its top side 102 being closest to the skin, is then slid through the slot 84 into the pocket so that the center of the IEAD is located under the acupoint 90. This implantation process is as easy as inserting a coin into a slot. With the IEAD 100 in place, the incision is sewn or otherwise closed, leaving the IEAD 100 under the skin 80 at the location of the acupoint 90 where electroacupuncture (EA) stimulation is desired.

Figure 1B:
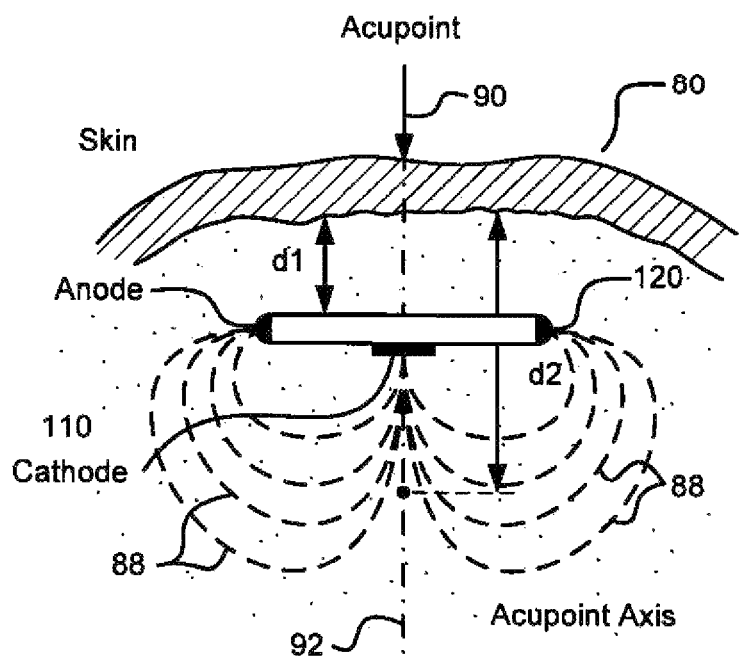
FIG. 1B shows a sectional view of an IEAD implanted at a selected acupoint, and illustrates the electric field gradient lines created when an electroacupuncture (EA) pulse is applied to the tissue through the central electrode and ring electrode attached to the bottom surface and perimeter edge, respectively, of the IEAD housing.

It should be noted that while FIG. 1B illustrates the acupoint 90 as being on the surface of the skin, the actual location where acupuncture treatment (whether it be administered through a needle, or through electroacupuncture (EA) stimulation) is most effective for purposes of the present invention is at a distance d2 below the skin surface along an axis line 92 extending orthogonally into the skin from the location on the skin where the acupoint 90 is indicated as being positioned. The distance d2 varies depending upon where the acupoint is located on the body. The depth d2 where EA stimulation is most effective for purposes of the present invention (to treat cardiovascular diseases, and more particularly to treat heart failure, CAD, myocardial ischemia, or angina) appears to be between about 6 to 10 mm below the skin surface in the location of an acupoint 90 located in the forearm (e.g., acupoint PC6).

FIG. 1B shows a sectional view of the IEAD 100 implanted so as to be centrally located under the skin at the selected acupoint 90, and over the acupoint axis line 92. Usually, for most patients, the IEAD 100 is implanted at a depth d1 of approximately 2-4 mm under the skin. The top side 102 of the IEAD is nearest to the skin 80 of the patient. The bottom side 106 of the IEAD, which is the side on which the central cathode electrode 110 resides, is farthest from the skin. Because the cathode electrode 110 is centered on the bottom of the IEAD, and because the IEAD 100 is implanted so as to be centered under the location on the skin where the acupoint 90 is located, the cathode 110 is also centered over the acupoint axis line 92.

FIG. 1B further illustrates the electric field gradient lines 88 that are created in the body tissue 86 surrounding the acupoint 90 and the acupoint axis line 92. (Note: for purposes herein, when reference is made to providing EA stimulation at a specified acupoint, it is understood that the EA stimulation is provided at a depth of approximately d2 below the location on the skin surface where the acupoint is indicated as being located.) As seen in FIG. 1B, the electric field gradient lines are strongest along a line that coincides with, or is near to, the acupoint axis line 92. It is thus seen that one of the main advantages of using a symmetrical electrode configuration that includes a centrally located electrode surrounded by an annular electrode is that the precise orientation of the IEAD within its implant location is not important. So long as one electrode is centered over the desired target location, and the other electrode surrounds the first electrode (e.g., as an annular electrode), a strong electric field gradient is created that is aligned with the acupoint axis line. This causes the EA stimulation current to flow along (or very near) the acupoint axis line 92, and will result in the desired EA stimulation in the tissue at a depth d2 below the acupoint location indicated on the skin.

FIG. 2 shows a plan view of the "cathode" side (or bottom side) of the IEAD 100. As seen in FIG. 2, the cathode electrode 110 appears as a circular electrode, centered on the cathode side, having a diameter D1. The IEAD housing has a diameter D2 and an overall thickness or width W2. For the preferred embodiment shown in these figures, D1 is about 4 mm, D2 is about 23 mm and W2 is a little over 2 mm (2.2 mm).

FIG. 2A shows a side view of the IEAD 100. The ring anode electrode 120, best seen in FIG. 2A, has a width W1 of about 1.0 mm, or approximately ½ of the width W2 of the IEAD.

FIG. 3 shows a plan view of the "skin" side (the top side) of the IEAD 100. As will be evident from subsequent figure descriptions, e.g., FIGS. 5A and 5B, the skin side of the IEAD 100 comprises a top plate 122 that is welded in place once the bottom case 124 has all of the electronic circuitry, and other components, placed inside of the housing.

FIG. 3A is a sectional view of the IEAD 100 of FIG. 1 taken along the line A-A of FIG. 3. Visible in this sectional view is the feed-through pin 130, including the distal end of the feed-through pin 130 attached to the ring anode electrode 120. Also visible in this section view is an electronic assembly 133 on which various electronic components are mounted, including a disc-shaped battery 132. FIG. 3A further illustrates how the top plate 122 is welded, or otherwise bonded, to the bottom case 124 in order to form the hermetically-sealed IEAD housing 100. (Note, in FIG. 3A, the "top" plate 122 is actually shown on the left side of the "bottom" case 124, which is shown on the right side. This is because the orientation of the drawing in FIG. 3A shows the IEAD 100 standing on its edge.)

Figure 4:
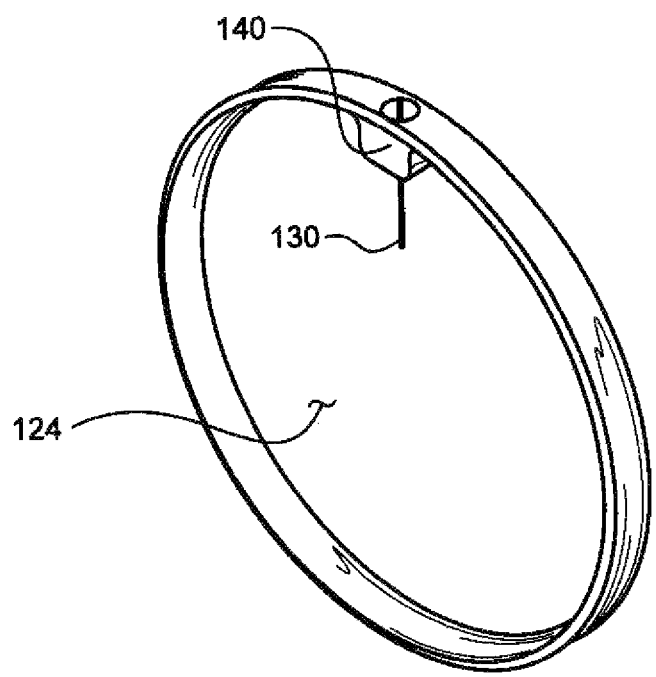
FIG. 4 is a perspective view of the IEAD housing, including a feed-through pin, before the electronic components are placed therein, and before being sealed with a "skin side" cover plate.

FIG. 4 shows a perspective view of the IEAD case 124, including the feed-through pin 130, before the electronic components are placed therein, and before being sealed with the "skin side" cover plate 122. The case 124 is similar to a shallow "can" without a lid, having a short side wall around its perimeter. Alternatively, the case 124 may be viewed as a short cylinder, closed at one end but open at the other. (Note, in the medical device industry the housing of an implanted device is often referred to as a "can".) The feed-through pin 130 passes through a segment of the wall of the case 124 that is at the bottom of a recess 140 formed in the wall. The use of this recess 140 to hold the feed-through pin 130 is a key feature of the invention because it keeps the temperature-sensitive portions of the feed-through assembly (those portions that could be damaged by excessive heat) away from the thermal shock and residual weld stress inflicted upon the case 124 when the cover plate 122 is welded thereto.

Figure 4A:
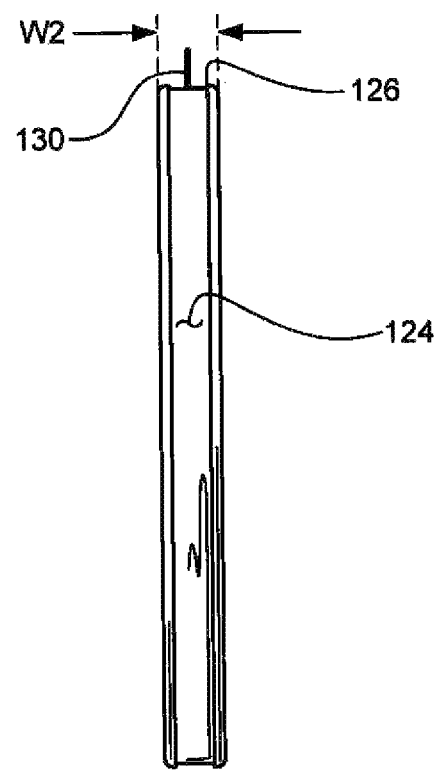
FIG. 4A is a side view of the IEAD housing of FIG. 4.

FIG. 4A is a side view of the IEAD case 124, and shows an annular rim 126 formed on both sides of the case 124. The ring anode electrode 120 fits between these rims 126 once the ring electrode 120 is positioned around the edge of the case 124. A silicone insulator layer 129 (see FIG. 7) is placed between the backside of the ring anode electrode 120 and the perimeter edge of the case 124 where the ring anode electrode 120 is placed around the edge of the case 124.

FIG. 5 shows a plan view of the empty IEAD case 124 shown in the perspective view of FIG. 4. An outline of the recess cavity 140 is also seen in FIG. 5, as is the feed-through pin 130. A bottom edge of the recess cavity 140 is located a distance D5 radially inward from the edge of the case 124. In one embodiment, the distance D5 is between about 2.0 to 2.5 mm. The feed-through pin 130, which is just a piece of solid wire, is shown in FIG. 5 extending radially outward from the case 124 above the recess cavity 140 and radially inward from the recess cavity towards the center of the case 124. The length of this feed-through pin 130 is trimmed, as needed, when a distal end (extending above the recess) is connected (welded) to the anode ring electrode 120 (passing through a hole in the ring electrode 120 prior to welding) and when a proximal end of the feed-through pin 130 is connected to an output terminal of the electronic assembly 133.

FIG. 5A depicts a sectional view of the IEAD housing 124 of FIG. 5 taken along the section line A-A of FIG. 5. FIG. 5B shows an enlarged view or detail of the portion of FIG. 5A that is encircled with the line B. Referring to FIGS. 5A and 5B jointly, it is seen that the feed-through pin 130 is embedded within an insulator material 136, which insulating material 136 has a diameter of D3. The feed-through pin assembly (which pin assembly comprises the combination of the pin 130 embedded into the insulator material 136) resides on a shoulder around an opening or hole formed in the bottom of the recess 140 having a diameter D4. For the embodiment shown in FIGS. 5A and 5B, the diameter D3 is 0.95-0.07 mm, where the −0.07 mm is a tolerance. (Thus, with the tolerance considered, the diameter D3 may range from 0.88 mm to 0.95 mm) The diameter D4 is 0.80 mm with a tolerance of −0.06 mm. (Thus, with the tolerance considered, the diameter D4 could range from 0.74 mm to 0.80 mm).

The feed-through pin 130 is preferably made of pure platinum 99.95%. A preferred material for the insulator material 136 is Ruby or alumina. The IEAD case 124, and the cover 122, are preferably made from titanium. The feed-through assembly, including the feed-through pin 130, ruby/alumina insulator 136 and the case 124 are hermetically sealed as a unit by gold brazing. Alternatively, active metal brazing can be used. (Active metal brazing is a form of brazing which allows metal to be joined to ceramic without metallization.)

The hermeticity of the sealed IEAD housing is tested using a helium leak test, as is common in the medical device industry. The helium leak rate should not exceed $1\times10^{-9}$ STD cc/sec at 1 atm pressure. Other tests are performed to verify the case-to-pin resistance (which should be at least $15\times10^{6}$ Ohms at 100 volts DC), the avoidance of dielectric breakdown or flashover between the pin and the case 124 at 400 volts AC RMS at 60 Hz and thermal shock.

One important advantage provided by the feed-through assembly shown in FIGS. 4A, 5, 5A and 5B is that the feed-through assembly made from the feed-through pin 130, the ruby insulator 136 and the recess cavity 140 (formed in the case material 124) may be fabricated and assembled before any other components of the IEAD 100 are placed inside of the IEAD case 124. This advantage greatly facilitates the manufacture of the IEAD device.

Turning next to FIG. 6, there is shown a perspective view of an electronic assembly 133. The electronic assembly 133 includes a multi-layer printed circuit (pc) board 138, or equivalent mounting structure, on which a battery 132 and various electronic components 134 are mounted. This assembly is adapted to fit inside of the empty bottom housing 124 of FIG. 4 and FIG. 5.

FIGS. 6A and 6B show a plan view and side view, respectively, of the electronic assembly 133 shown in FIG. 6. The electronic components are assembled and connected together so as to perform the circuit functions needed for the IEAD 100 to perform its intended functions. These circuit functions are explained in more detail below under the sub-heading "Electrical Design". Additional details associated with these functions may also be found in many of the co-pending patent applications referenced above in Paragraph [0001].

FIG. 7 shows an exploded view of the complete IEAD 100, illustrating its main constituent parts. As seen in FIG. 7, the IEAD 100 includes, starting on the right and going left, a cathode electrode 110, a ring anode electrode 120, an insulating layer 129, the bottom case 124 (the "can" portion of the IEAD housing, and which includes the feed-through pin 130 which passes through an opening in the bottom of the recess 140 formed as part of the case, but wherein the feed-through pin 130 is insulated and does not make electrical contact with the metal case 124 by the ruby insulator 136), the electronic assembly 133 (which includes the battery 132 and various electronic components 134 mounted on a pc board 138) and the cover plate 122. The cover plate 122 is welded to the edge of the bottom case 124 using laser beam welding, or some equivalent process, as one of the final steps in the assembly process.

Other components included in the IEAD assembly, but not necessarily shown or identified in FIG. 7, include adhesive patches for bonding the battery 132 to the pc board 138 of the electronic assembly 133, and for bonding the electronic assembly 133 to the inside of the bottom of the case 124. To prevent high temperature exposure of the battery 132 during the assembly process, conductive epoxy is used to connect a battery terminal to the pc board 138. Because the curing temperature of conductive epoxy is 125° C., the following process is used: (a) first cure the conductive epoxy of a battery terminal ribbon to the pc board without the battery, (b) then glue the battery to the pc board using room temperature cure silicone, and (c) laser tack weld the connecting ribbon to the battery.

Also not shown in FIG. 7 is the manner of connecting the proximal end of the feed-through pin 130 to the pc board 138, and connecting a pc board ground pad to the case 124. A preferred method of making these connections is to use conductive epoxy and conductive ribbons, although other connection methods known in the art may also be used.

Further shown in FIG. 7 is a layer of silicon molding 125 that is used to cover all surfaces of the entire IEAD 100 except for the anode ring electrode 120 and the circular cathode electrode 110. An overmodling process is used to accomplish this, although overmolding using silicone LSR 70 (curing temperature of 120° C.) with an injection moldling process cannot be used. Overmolding processes that may be used include: (a) molding a silicone jacket and gluing the jacket onto the case using room temperature cure silicone (RTV) inside of a mold, and curing at room temperature; (b) injecting room temperature cure silicone in a PEEK or Teflon® mold (silicone will not stick to the Teflon® or PEEK material); or (c) dip coating the IEAD 100 in room temperature cure silicone while masking the electrode surfaces that are not to be coated. (Note: PEEK is a well known semicrystalline thermoplastic with excellent mechanical and chemical resistance properties that are retained at high temperatures.)

When assembled, the insulating layer 129 is positioned underneath the ring anode electrode 120 so that the anode electrode does not short to the case 124. The only electrical connection made to the anode electrode 120 is through the distal tip of the feed-through pin 130. The electrical contact with the cathode electrode 110 is made through the case 124. However, because the entire IEAD is coated with a layer of silicone molding 125, except for the anode ring electrode 120 and the circular cathode electrode 110, all stimulation current generated by the IEAD 100 must flow between the exposed surfaces of the anode and cathode.

It is noted that while the preferred configuration described herein uses a ring anode electrode 120 placed around the edges of the IEAD housing, and a circular cathode electrode 110 placed in the center of the cathode side of the IEAD case 124, such an arrangement could be reversed, i.e., the ring electrode could be the cathode, and the circular electrode could be the anode.

Moreover, the location and shape of the electrodes may be configured differently than is shown in the one preferred embodiment described above in connection with FIGS. 1, and 2-7. For example, the ring anode electrode 120 need not be placed around the perimeter of the device, but such electrode may be a flat circumferential electrode that assumes different shapes (e.g., round or oval) that is placed on the bottom or on the top surface of the IEAD so as to surround the central electrode. Further, for some embodiments, the surfaces of the anode and cathode electrodes may have convex surfaces.

It is also noted that while one preferred embodiment has been disclosed herein that incorporates a round, or short cylindrical-shaped housing, also referred to as a coin-shaped housing, the invention does not require that the case 124 (which may also be referred to as a "container"), and its associated cover plate 122, be round. The case could just as easily be an oval-shaped, rectangular-shaped (e.g., square with smooth corners), polygonal-shaped (e.g., hexagon-, octagon-, pentagon-shaped), button-shaped (with convex top or bottom for a smoother profile) device. Any of these alternate shapes, or others, would still permit the basic principles of the invention to be used to help protect a feed-through assembly from being exposed to excessive heat during assembly, and to allow the thin device to provide the benefits described herein related to its manufacture, implantation and use. For example, as long as the device remains relatively thin, e.g., no more than about 2-3 mm, and does not have a maximum linear dimension greater than about 25 mm, then the device can be easily implanted in a pocket over the tissue area where the selected acupuoint(s) is located. As long as there is a recess in the wall around the perimeter of the case wherein the feed-through assembly may be mounted, which recess effectively moves the wall or edge of the case inwardly into the housing a safe thermal distance, as well as a safe residual weld stress distance, from the perimeter wall where a hermetically-sealed weld occurs, the principles of the invention apply.

Further, it should be noted that while the preferred configuration of the IEAD described herein utilizes a central electrode on one of its surfaces that is round, having a diameter of nominally 4 mm, such central electrode need not necessarily be round. It could be oval shaped, polygonal-shaped, or shaped otherwise, in which case its size is best defined by its maximum width, which will generally be no greater than about 7 mm.

Figure 7A:
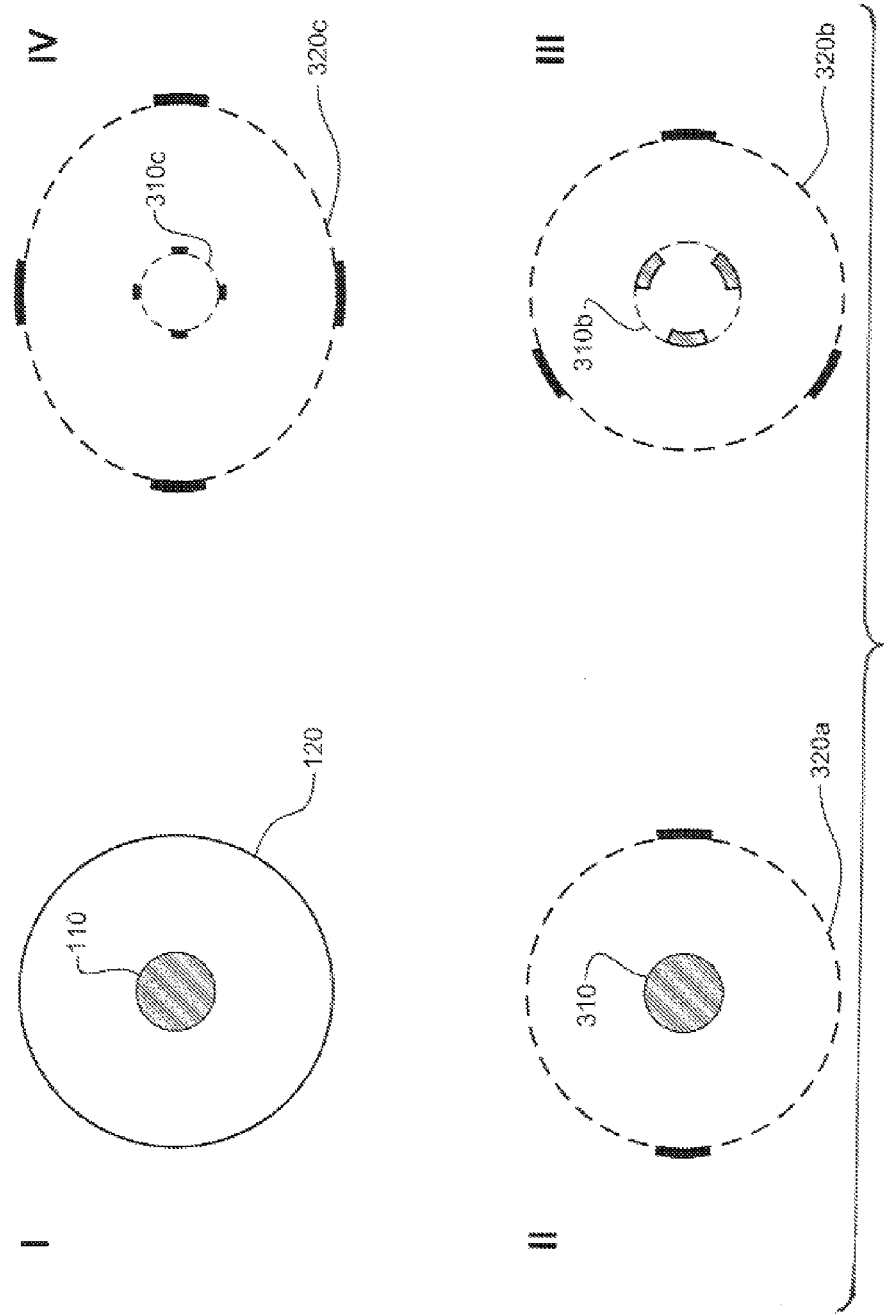
FIG. 7A schematically illustrates a few alternative electrode configurations that may be used with the invention.

Finally, it is noted that the electrode arrangement may be modified somewhat, and the desired attributes of the invention may still be achieved. For example, as indicated previously, one preferred electrode configuration for use with the invention utilizes a symmetrical electrode configuration, e.g., an annular electrode of a first polarity that surrounds a central electrode of a second polarity. Such a symmetrical electrode configuration makes the implantable electroacupuncture device (IEAD) relatively immune to being implanted in an improper orientation relative to the body tissue at the selected acupoint(s) that is being stimulated. However, an electrode configuration that is not symmetrical may still be used and many of the therapeutic effects of the invention may still be achieved. For example, two spaced-apart electrodes on a bottom surface of the housing, one of a first polarity, and a second of a second polarity, could still, when oriented properly with respect to a selected acupoint tissue location, provide some desired therapeutic results FIG. 7A schematically illustrates a few alternative electrode configurations that may be used with the invention. The electrode configuration schematically shown in the upper left corner of FIG. 7A, identified as "I", schematically illustrates one central electrode 110 surrounded by a single ring electrode 120. This is one of the preferred electrode configurations that has been described previously in connection, e.g., with the description of FIGS. 1, 1A, 1B and 7, and is presented in FIG. 7A for reference and comparative purposes.

In the lower left corner of FIG. 7A, identified as "II", an electrode/array configuration is schematically illustrated that has a central electrode 310 of a first polarity surrounded by an electrode array 320a of two electrodes of a second polarity. When the two electrodes (of the same polarity) in the electrode array 320a are properly aligned with the body tissue being stimulated, e.g., aligned with the longitudinal axis of the limb 80 (see FIG. 1A) wherein the IEAD is implanted, then such electrode configuration can stimulate the body tissue at or near the desired acupoint(s) with the same, or almost the same, efficacy as can the electrode configuration I (upper right corner of FIG. 7A).

Note, as has already been described above, the phrase "electrode or electrode array," or "electrodes or electrode arrays," may also be referred to herein as "electrode/array" or "electrodes/arrays," respectively. For the ease of explanation, when an electrode array is referred to herein that comprises a plurality (two or more) of individual electrodes of the same polarity, the individual electrodes of the same polarity within the electrode array may also be referred to as "individual electrodes", "segments" of the electrode array, "electrode segments", or just "segments".

In the lower right corner of FIG. 7A, identified as "III", en electrode configuration is schematically illustrated that has a central electrode/array 310b of three electrode segments of a first polarity surrounded by an electrode array 320b of three electrode segments of a second polarity. As shown in FIG. 7A-III, the three electrode segments of the electrode array 320b are symmetrically positioned within the array 320b, meaning that they are positioned more or less equidistant from each other. However, a symmetrical positioning of the electrode segments within the array is not necessary to stimulate the body tissue at the desired acupoint(s) with some efficacy.

In the upper right corner of FIG. 7A, identified as "IV", an electrode/array configuration is schematically illustrated that has a central electrode array 310c of a first polarity surrounded by an electrode array 320c of four electrode segments of a second polarity. The four electrode segments of the electrode array 320c are arranged symmetrically in a round or oval-shaped array. The four electrode segments of the electrode array 310b are likewise arranged symmetrically in a round or oval-shaped array. Again, however, while preferred for many configurations, the use of a symmetrical electrode/array, whether as a central electrode array 310 or as a surrounding electrode/array 320, is not required in all configurations.

The electrode configurations I, II, III and IV shown schematically in FIG. 7A are only representative of a few electrode configurations that may be used with the present invention. Further, it is to be noted that the central electrode/array 310 need not have the same number of electrode segments as does the surrounding electrode/array 320. Typically, the central electrode/array 310 of a first polarity will be a single electrode; whereas the surrounding electrode/array 320 of a second polarity may have n individual electrode segments, where n is an integer that can vary from 1, 2, 3, ... n. Thus, for a circumferential electrode array where n=4, there are four electrode segments of the same polarity arranged in circumferential pattern around a central electrode/array. If the circumferential electrode array with n=4 is a symmetrical electrode array, then the four electrode segments will be spaced apart equally in a circumferential pattern around a central electrode/array. When n=1, the circumferential electrode array reduces to a single circumferential segment or a single annular electrode that surrounds a central electrode/array.

Additionally, the polarities of the electrode/arrays may be selected as needed. That is, while the central electrode/array 310 is typically a cathode (−), and the surrounding electrode/array 320 is typically an anode (+), these polarities may be reversed.

It should be noted that the shape of the circumferential electrode/array, whether circular, oval, or other shape, need not necessarily be the same shape as the IEAD housing, unless the circumferential electrode/array is attached to a perimeter edge of the IEAD housing. The IEAD housing may be round, or it may be oval, or it may have a polygon shape, or other shape, as needed to suit the needs of a particular manufacturer and/or patient.

Additional electrode configurations, both symmetrical electrode configurations and non-symmetrical electrode configurations, that may be used with an EA stimulation device as described herein, are described in Appendices A and B.

Electrical Design

Next, with reference to FIGS. 8A-14, the electrical design and operation of the circuits employed within the IEAD 100 will be described. More details associated with the design of the electrical circuits described herein may be found in the following previously-filed U.S. Provisional Patent Applications, which applications are incorporated herein by reference: (1) Appl. No. 61/575,869, filed Aug. 30, 2012, entitled Implantable Electroacupuncture Device and Method For Reducing Hypertension; (2) Appl. No. 61/609,875, filed Mar. 12, 2012, entitled Boost Converter Output Control For Implantable Electroacupuncture Device; (3) Appl. No. 61/672,257, filed Jul. 16, 2012, entitled Boost Converter Circuit Surge Control For Implantable Electroacupuncture Device Using Digital Pulsed Shutdown; (4) Appl. No. 61/672,661, filed Jul. 17, 2012, entitled Smooth Ramp-Up Stimulus Amplitude Control For Implantable Electroacupuncture Device; and (5) Appl. No. 61/674,691, filed Jul. 23, 2012, entitled Pulse Charge Delivery Control In An Implantable Electroacupuncture Device.

Figure 8A:
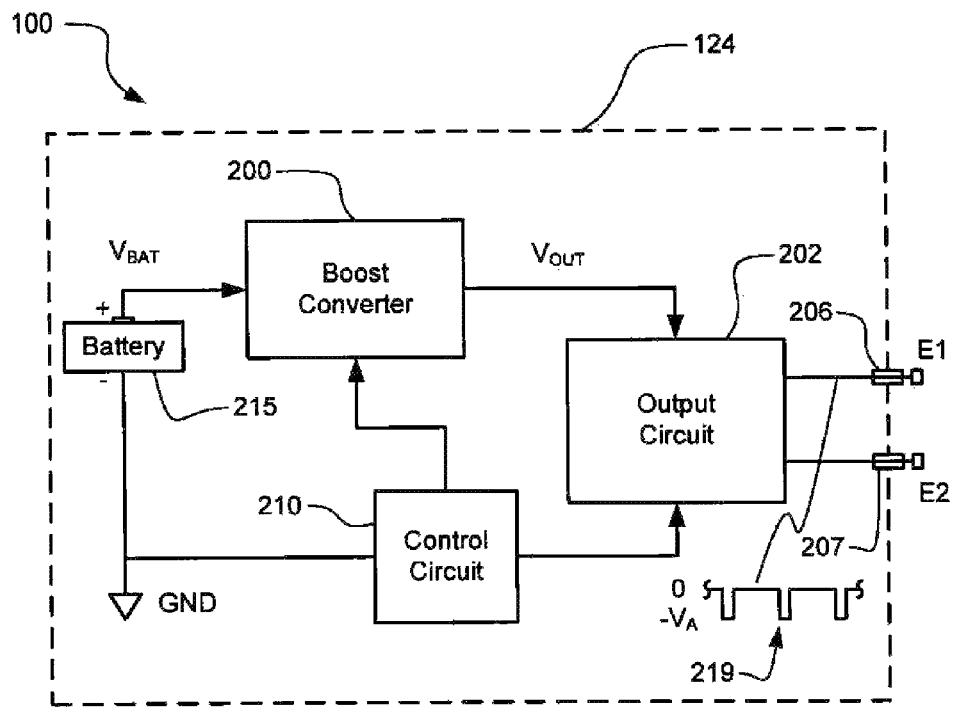
FIG. 8A illustrates a functional block diagram of the electronic circuits used within an IEAD of the type described herein.

FIG. 8A shows a functional block diagram of an implantable electroacupuncture device (IEAD) 100 made in accordance with the teachings disclosed herein. As seen in FIG. 8A, the IEAD 100 uses an implantable battery 215 having a battery voltage $V_{BAT}$. Also included within the IEAD 100 is a Boost Converter circuit 200, an Output Circuit 202 and a Control Circuit 210. The battery 115, boost converter circuit 200, output circuit 202 and control circuit 210 are all housed within an hermetically sealed housing 124.

As controlled by the control circuit 210, the output circuit 202 of the IEAD 100 generates a sequence of stimulation pulses that are delivered to electrodes E1 and E2, through feed-through terminals 206 and 207, respectively, in accordance with a prescribed stimulation regimen. A coupling capacitor $C_C$ is also employed in series with at least one of the feed-through terminals 206 or 207 to prevent DC (direct current) current from flowing into the patient's body tissue.

Figure 15A:
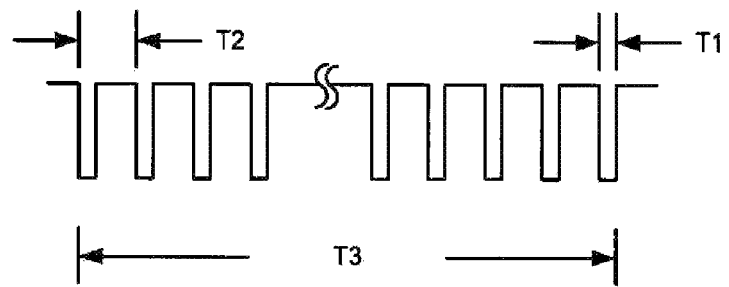
FIG. 15A shows a timing waveform diagram of representative EA stimulation pulses generated by the IEAD device during a stimulation session.

As explained more fully below in connection with the description of FIGS. 15A and 15B, the prescribed stimulation regimen comprises a continuous stream of stimulation pulses having a fixed amplitude, e.g., $V_A$ volts, a fixed pulse width, e.g., 0.5 millisecond, and at a fixed frequency, e.g., 2 Hz, during each stimulation session. The stimulation session, also as part of the stimulation regimen, is generated at a very low duty cycle, e.g., for 30 minutes once each week.

In one preferred embodiment, the electrodes E1 and E2 form an integral part of the housing 124. That is, electrode E2 may comprise a circumferential anode electrode that surrounds a cathode electrode E1. The cathode electrode E1, for the embodiment described here, is electrically connected to the case 124 (thereby making the feed-through terminal 206 unnecessary).

In a second preferred embodiment, particularly well-suited for implantable electrical stimulation devices, the anode electrode E2 is electrically connected to the case 124 (thereby making the feed-through terminal 207 unnecessary). The cathode electrode E1 is electrically connected to the circumferential electrode that surrounds the anode electrode E2. That is, the stimulation pulses delivered to the target tissue location (i.e., to the selected acupoint) through the electrodes E1 and E2 are, relative to a zero volt ground (GND) reference, negative stimulation pulses, as shown in the waveform diagram near the lower right hand corner of FIG. 8A.

Thus, in the embodiment described in FIG. 8A, it is seen that during a stimulation pulse the electrode E2 functions as an anode, or positive (+) electrode, and the electrode E1 functions as a cathode, or negative (−) electrode.

The battery 115 provides all of the operating power needed by the EA device 100. The battery voltage $V_{BAT}$ is not the optimum voltage needed by the circuits of the EA device, including the output circuitry, in order to efficiently generate stimulation pulses of amplitude, e.g., $-V_A$ volts. The amplitude $V_A$ of the stimulation pulses is typically many times greater than the battery voltage $V_{BAT}$. This means that the battery voltage must be "boosted", or increased, in order for stimulation pulses of amplitude $V_A$ to be generated. Such "boosting" is done using the boost converter circuit 200. That is, it is the function of the Boost Converter circuit 200 to take its input voltage, $V_{BAT}$, and convert it to another voltage, e.g., $V_{OUT}$, which voltage $V_{OUT}$ is needed by the output circuit 202 in order for the IEAD 100 to perform its intended function.

The IEAD 100 shown in FIG. 8A, and packaged as described above in connection with FIGS. 1-7, advantageously provides a tiny self-contained, coin-sized stimulator that may be implanted in a patient at or near a specified acupoint in order to favorably treat a condition or disease of a patient. The coin-sized stimulator advantageously applies electrical stimulation pulses at very low levels and duty cycles in accordance with specified stimulation regimens through electrodes that form an integral part of the housing of the stimulator. A tiny battery inside of the coin-sized stimulator provides enough energy for the stimulator to carry out its specified stimulation regimen over a period of several years. Thus, the coin-sized stimulator, once implanted, provides an unobtrusive, needleless, long-lasting, safe, elegant and effective mechanism for treating certain conditions and diseases that have long been treated by acupuncture or electroacupuncture.

Figure 8B:
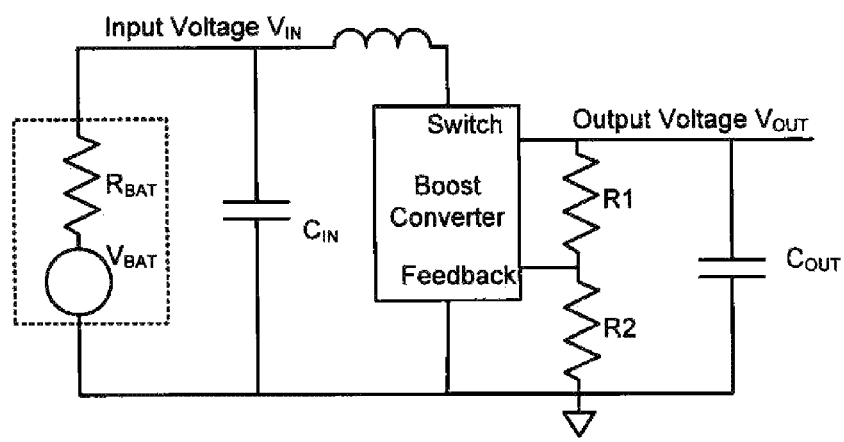
FIG. 8B shows a basic boost converter circuit configuration, and is used to model how the impedance of the battery $R_{BAT}$ can affect its performance.

A boost converter integrated circuit (IC) typically draws current from its power source in a manner that is proportional to the difference between the actual output voltage $V_{OUT}$ and a set point output voltage, or feedback signal. A representative boost converter circuit that operates in this manner is shown in FIG. 8B. At boost converter start up, when the actual output voltage is low compared to the set point output voltage, the current drawn from the power source can be quite large. Unfortunately, when batteries are used as power sources, they have internal voltage losses (caused by the battery's internal impedance) that are proportional to the current drawn from them. This can result in under voltage conditions when there is a large current demand from the boost converter at start up or at high instantaneous output current. Current surges and the associated under voltage conditions can lead to undesired behavior and reduced operating life of an implanted electroacupuncture device.

In the boost converter circuit example shown in FIG. 8A, the battery is modeled as a voltage source with a simple series resistance. With reference to the circuit shown in FIG. 8A, when the series resistance $R_{BAT}$ is small (5 Ohms or less), the boost converter input voltage $V_{IN}$, output voltage $V_{OUT}$ and current drawn from the battery, $I_{BAT}$, typically look like the waveform shown in FIG. 9A, where the horizontal axis is time, and the vertical axis on the left is voltage, and the vertical axis of the right is current.

Figure 9A:
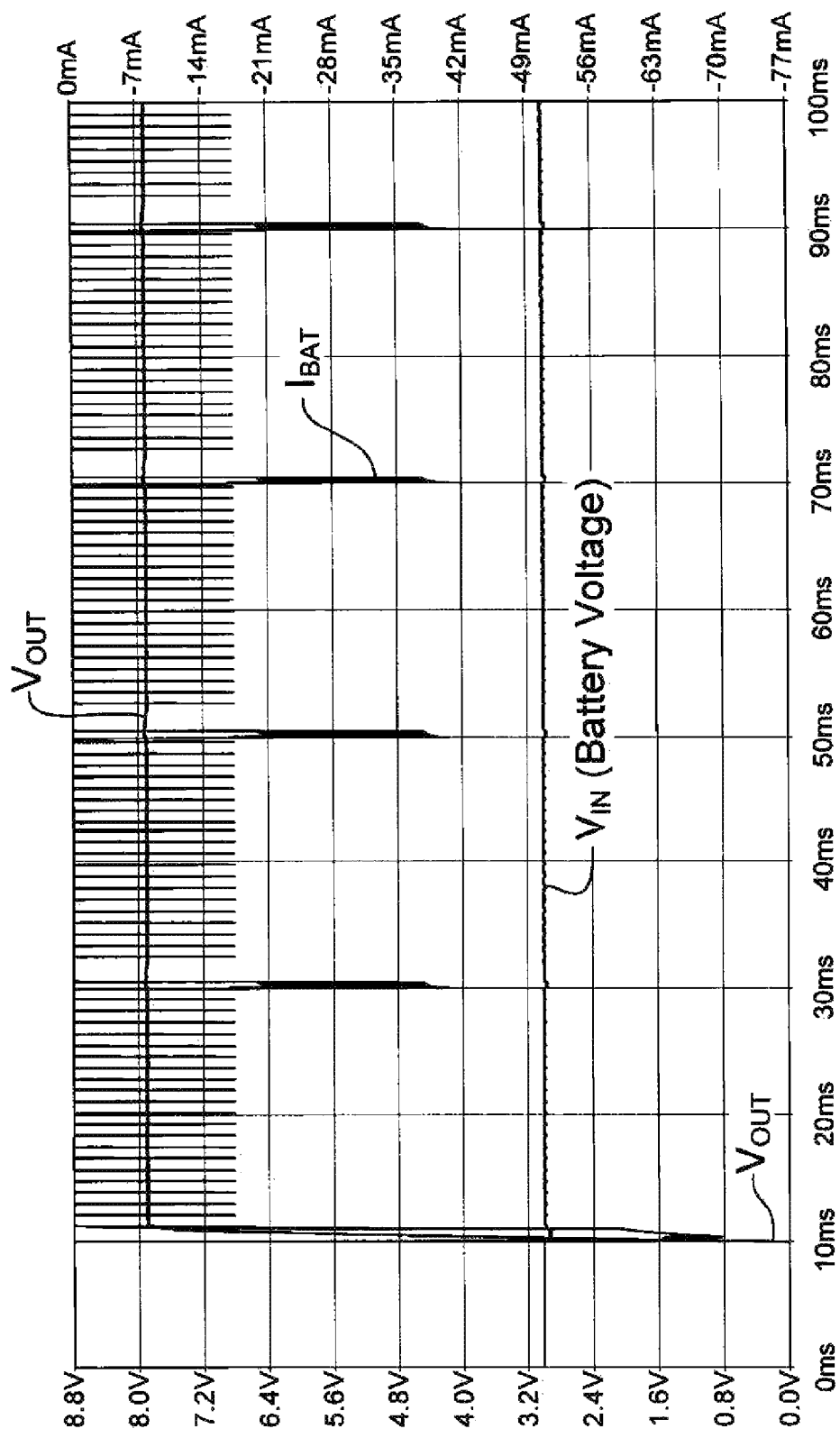
FIG. 9A illustrates a typical voltage and current waveform for the circuit of FIG. 8 when the battery impedance $R_{BAT}$ is small.

Referring to the waveform in FIG. 9A, at boost converter startup (10 ms), there is 70 mA of current drawn from the battery with only ~70 mV of drop in the input voltage $V_{IN}$. Similarly, the instantaneous output current demand for electro-acupuncture pulses draws up to 40 mA from the battery with an input voltage drop of ~40 mV.

Figure 9B:
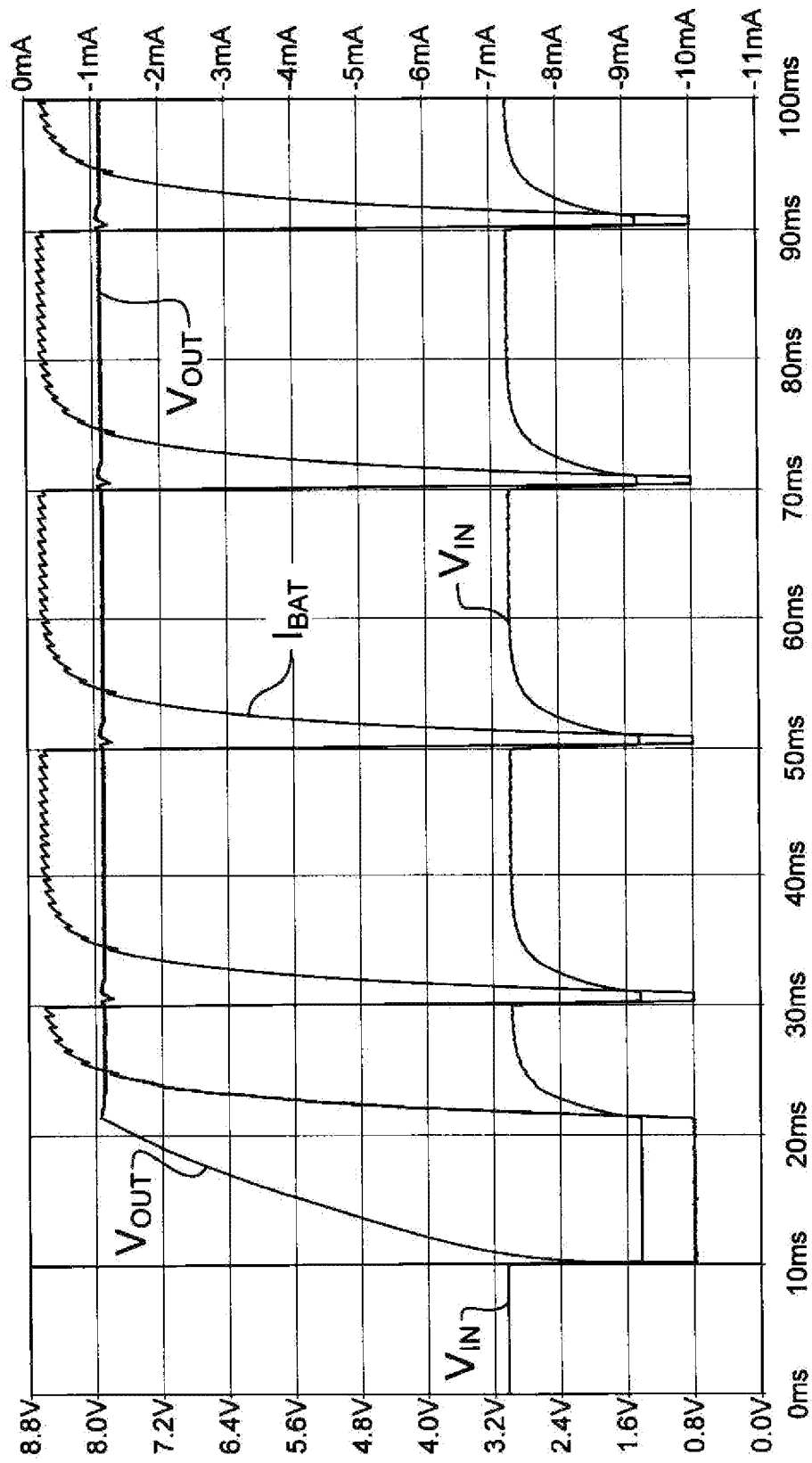
FIG. 9B shows the voltage and current waveform for the circuit of FIG. 8B when the battery impedance $R_{BAT}$ is large.

Disadvantageously, however, a battery with higher internal impedance (e.g., 160 Ohms), cannot source more than a milliampere or so of current without a significant drop in output voltage. This problem is depicted in the timing waveform diagram shown in FIG. 9B. In FIG. 9B, as in FIG. 9A, the horizontal axis is time, the left vertical axis is voltage, and the right vertical axis is current.

As seen in FIG. 9B, as a result of the higher internal battery impedance, the voltage at the battery terminal ($V_{IN}$) is pulled down from 2.9 V to the minimum input voltage of the boost converter (~1.5 V) during startup and during the instantaneous output current load associated with electro-acupuncture stimulus pulses. The resulting drops in output voltage $V_{OUT}$ are just not acceptable in any type of circuit except an uncontrolled oscillator circuit.

Also, it should be noted that although the battery used in the boost converter circuit is modeled in FIG. 8B as a simple series resistor, battery impedance can arise from the internal design, battery electrode surface area and different types of electrochemical reactions. All of these contributors to battery impedance can cause the voltage of the battery at the battery terminals to decrease as the current drawn from the battery increases.

In a suitably small and thin implantable electroacupuncture device (IEAD) of the type disclosed herein, it is desired to use a higher impedance battery in order to assure a small and thin device, keep costs low, and/or to have low self-discharge rates. The battery internal impedance also typically increases as the battery discharges. This can limit the service life of the device even if a new battery has acceptably low internal impedance. Thus, it is seen that for the IEAD 100 disclosed herein to reliably perform its intended function over a long period of time, a circuit design is needed for the boost converter circuit that can manage the instantaneous current drawn from $V_{IN}$ of the battery. Such current management is needed to prevent the battery's internal impedance from causing $V_{IN}$ to drop to unacceptably low levels as the boost converter circuit pumps up the output voltage $V_{OUT}$ and when there is high instantaneous output current demand, as occurs when EA stimulation pulses are generated.

Figure 10:
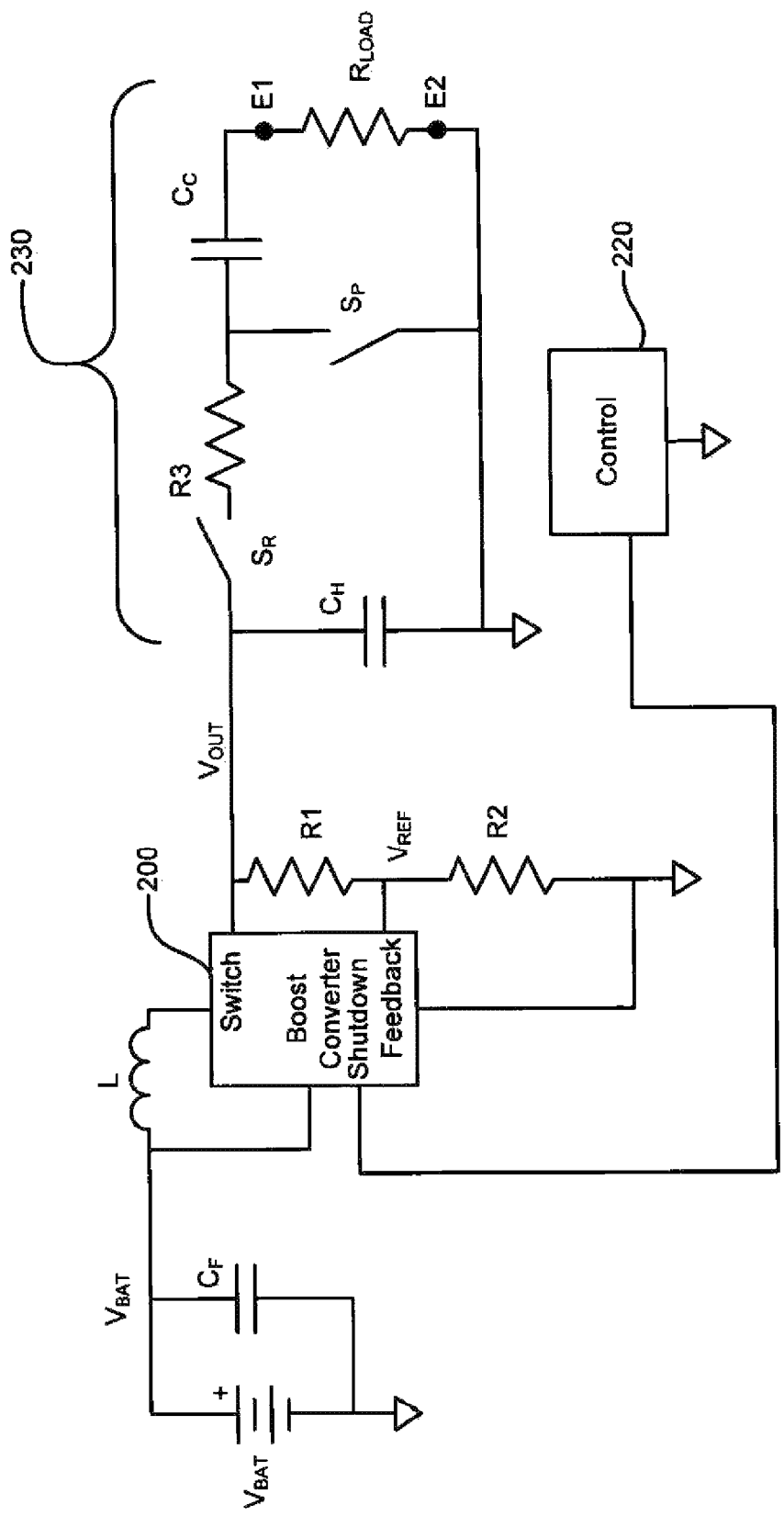
FIG. 10 shows one preferred boost converter circuit and a functional pulse generation circuit configuration for use within the IEAD.

To provide this needed current management, the IEAD 100 disclosed herein employs electronic circuitry as shown in FIG. 10, or equivalents thereof. Similar to what is shown in FIG. 8B, the circuitry of FIG. 10 includes a battery, a boost converter circuit 200, an output circuit 230, and a control circuit 220. The control circuit 220 generates a digital control signal that is used to duty cycle the boost converter circuit 200 ON and OFF in order to limit the instantaneous current drawn from the battery. That is, the digital control signal pulses the boost converter ON for a short time, but then shuts the boost converter down before a significant current can be drawn from the battery. In conjunction with such pulsing, an input capacitance $C_F$ is used to reduce the ripple in the input voltage $V_{IN}$. The capacitor $C_F$ supplies the high instantaneous current for the short time that the boost converter is ON and then recharges more slowly from the battery during the interval that the boost converter is OFF.

In the circuitry shown in FIG. 10, it is noted that the output voltage $V_{OUT}$ generated by the boost converter circuit 200 is set by the reference voltage $V_{REF}$ applied to the set point or feedback terminal of the boost converter circuit 200. For the configuration shown in FIG. 10, $V_{REF}$ is proportional to the output voltage $V_{OUT}$, as determined by the resistor dividing network of R1 and R2.

The switches $S_P$ and $S_R$, shown in FIG. 10 as part of the output circuit 230, are also controlled by the control circuit 220. These switches are selectively closed and opened to form the EA stimulation pulses applied to the load, $R_{LOAD}$. Before a stimulus pulse occurs, switch $S_R$ is closed sufficiently long for the circuit side of coupling capacitor $C_C$ to be charged to the output voltage, $V_{OUT}$. The tissue side of $C_C$ is maintained at 0 volts by the cathode electrode E2, which is maintained at ground reference. Then, for most of the time between stimulation pulses, both switches $S_R$ and $S_P$ are kept open, with a voltage approximately equal to the output voltage $V_{OUT}$ appearing across the coupling capacitor $C_C$.

At the leading edge of a stimulus pulse, the switch $S_P$ is closed, which immediately causes a negative voltage $-V_{OUT}$ to appear across the load, $R_{LOAD}$, causing the voltage at the anode E1 to also drop to approximately $-V_{OUT}$, thereby creating the leading edge of the stimulus pulse. This voltage starts to decay back to 0 volts as controlled by an RC (resistor-capacitance) time constant that is long compared with the desired pulse width. At the trailing edge of the pulse, before the voltage at the anode E1 has decayed very much, the switch $S_P$ is open and the switch $S_R$ is closed. This action causes the voltage at the anode E1 to immediately (relatively speaking) return to 0 volts, thereby defining the trailing edge of the pulse. With the switch $S_R$ closed, the charge on the circuit side of the coupling capacitor $C_C$ is allowed to charge back to $V_{OUT}$ within a time period controlled by a time constant set by the values of capacitor $C_C$ and resistor R3. When the circuit side of the coupling capacitor $C_C$ has been charged back to $V_{OUT}$, then switch $S_R$ is opened, and both switches $S_R$ and $S_P$ remain open until the next stimulus pulse is to be generated. Then the process repeats each time a stimulus pulse is to be applied across the load.

Thus, it is seen that in one embodiment of the electronic circuitry used within the IEAD 100, as shown in FIG. 10, a boost converter circuit 200 is employed which can be shut down with a control signal. The control signal is ideally a digital control signal generated by a control circuit 220 (which may be realized using a microprocessor or equivalent circuit). The control signal is applied to the low side (ground side) of the boost converter circuit 200 (identified as the "shutdown" terminal in FIG. 10). A capacitor $C_F$ supplies instantaneous current for the short ON time that the control signal enables the boost converter circuit to operate. And, the capacitor CF is recharged from the battery during the relatively long OFF time when the control signal disables the boost converter circuit.

Figure 11:
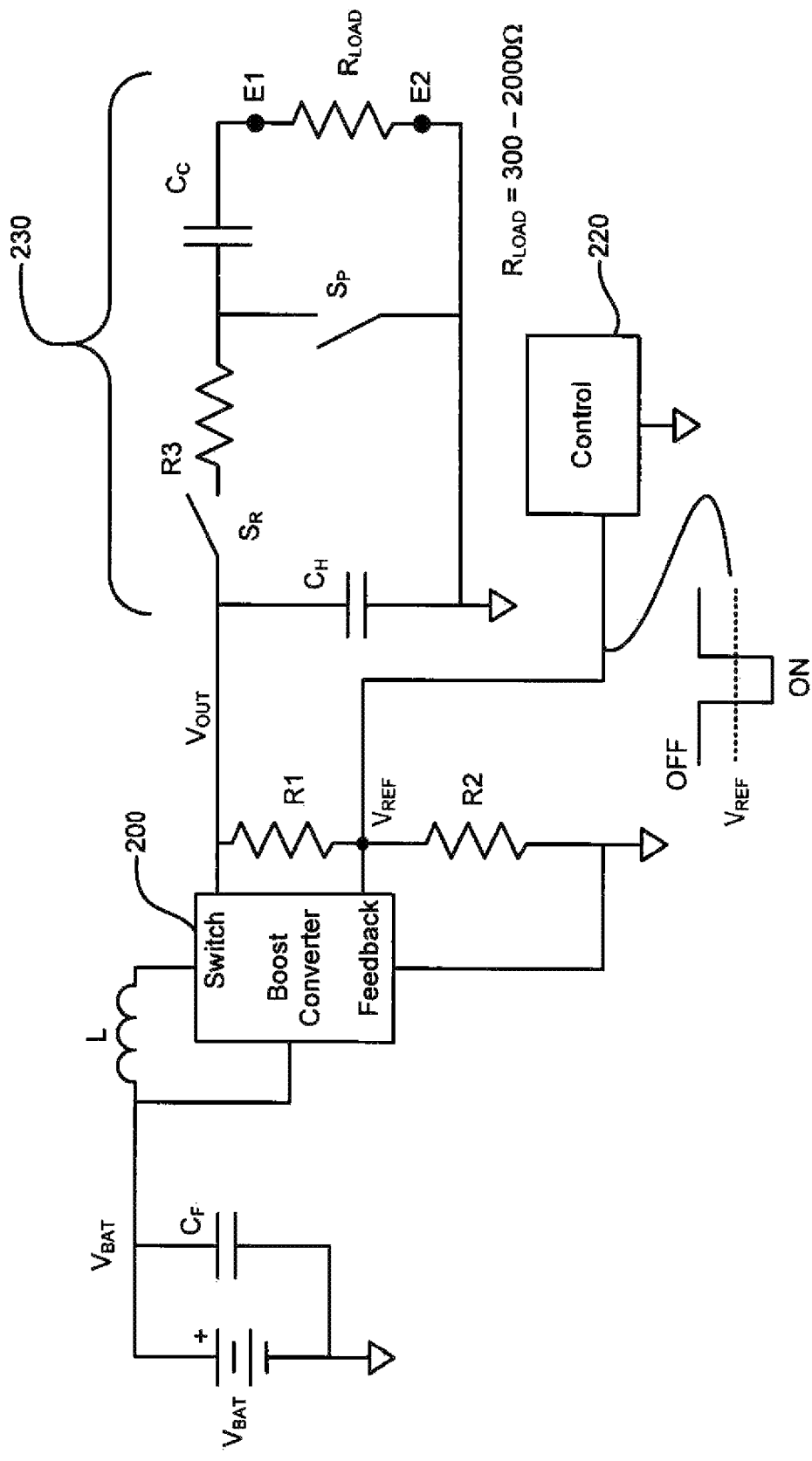
FIG. 11 shows an alternate boost converter circuit configuration and a functional pulse generation circuit for use within the IEAD.

An alternate embodiment of the electronic circuitry that may be used within the IDEA 100 is shown in FIG. 11. This circuit is in most respects the same as the circuitry shown in FIG. 10. However, in this alternate embodiment shown in FIG. 11, the boost converter circuit 200 does not have a specific shut down input control. Rather, as seen in FIG. 11, the boost converter circuit is shut down by applying a control voltage to the feedback input of the boost converter circuit 200 that is higher than $V_{REF}$. When this happens, i.e., when the control voltage applied to the feedback input is greater than $V_{REF}$, the boost converter will stop switching and draws little or no current from the battery. The value of $V_{REF}$ is typically a low enough voltage, such as a 1.2 V band-gap voltage, that a low level digital control signal can be used to disable the boost converter circuit. To enable the boost converter circuit, the control signal can be set to go to a high impedance, which effectively returns the node at the $V_{REF}$ terminal to the voltage set by the resistor divider network formed from R1 and R2. Alternatively the control signal can be set to go to a voltage less than $V_{REF}$.

A low level digital control signal that performs this function of enabling (turning ON) or disabling (turning OFF) the boost converter circuit is depicted in FIG. 11 as being generated at the output of a control circuit 220. The signal line on which this control signal is present connects the output of the control circuit 220 with the $V_{REF}$ node connected to the feedback input of the boost converter circuit. This control signal, as suggested by the waveform shown in FIG. 11, varies from a voltage greater than $V_{REF}$, thereby disabling or turning OFF the boost converter circuit, to a voltage less than $V_{REF}$, thereby enabling or turning the boost converter circuit ON.

Figure 12:
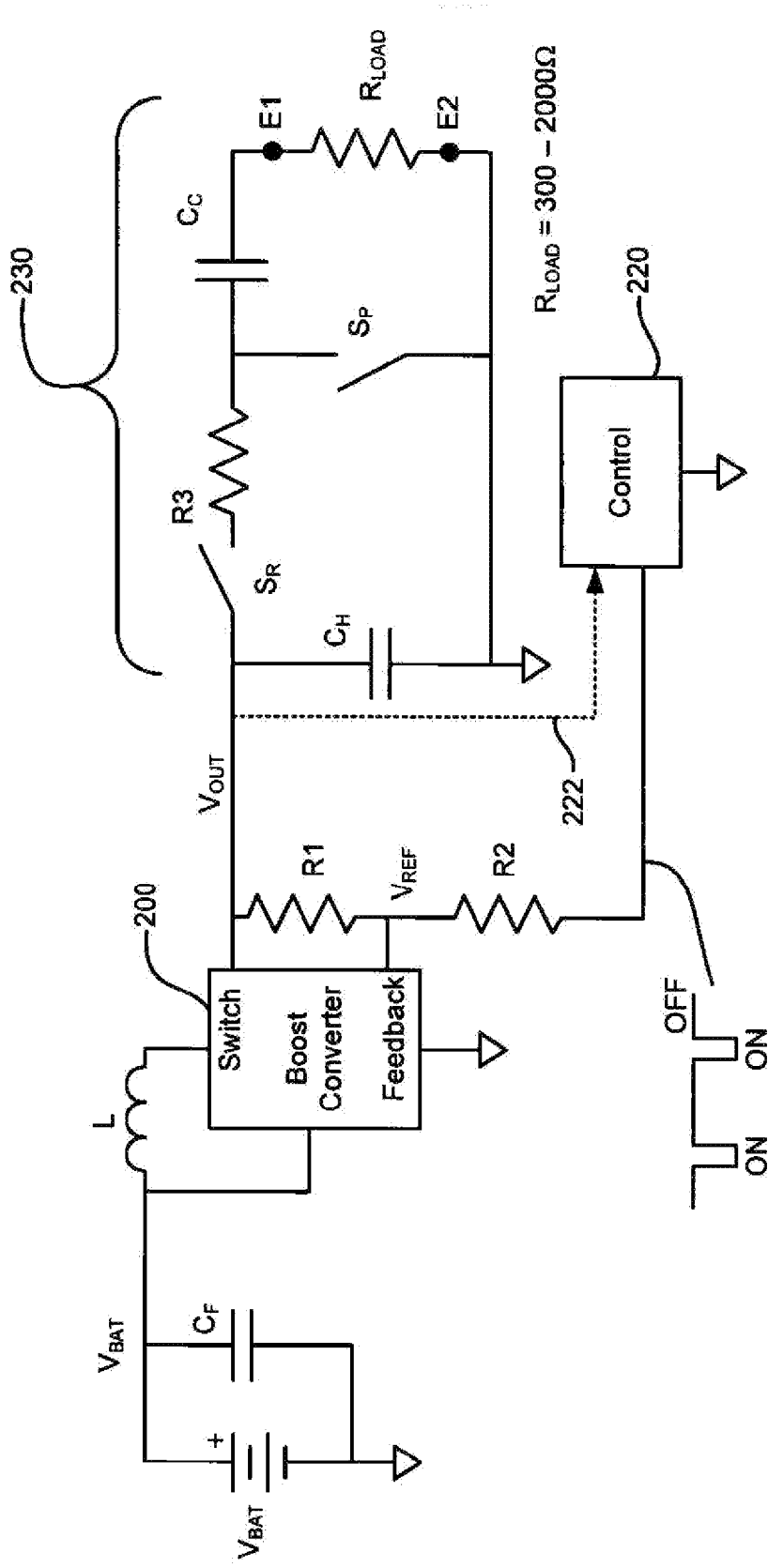
FIG. 12 shows a refinement of the circuit configuration of FIG. 11.

A refinement to the alternate embodiment shown in FIG. 11 is to use the control signal to drive the low side of R2 as shown in FIG. 12. That is, as shown in FIG. 12, the boost converter circuit 200 is shut down when the control signal is greater than $V_{REF}$ and runs when the control signal is less than $V_{REF}$. A digital control signal can be used to perform this function by switching between ground and a voltage greater than $V_{REF}$. This has the additional possibility of delta-sigma modulation control of $V_{OUT}$ if a measurement of the actual $V_{OUT}$ is available for feedback, e.g., using a signal line 222, to the controller.

Figure 13A:
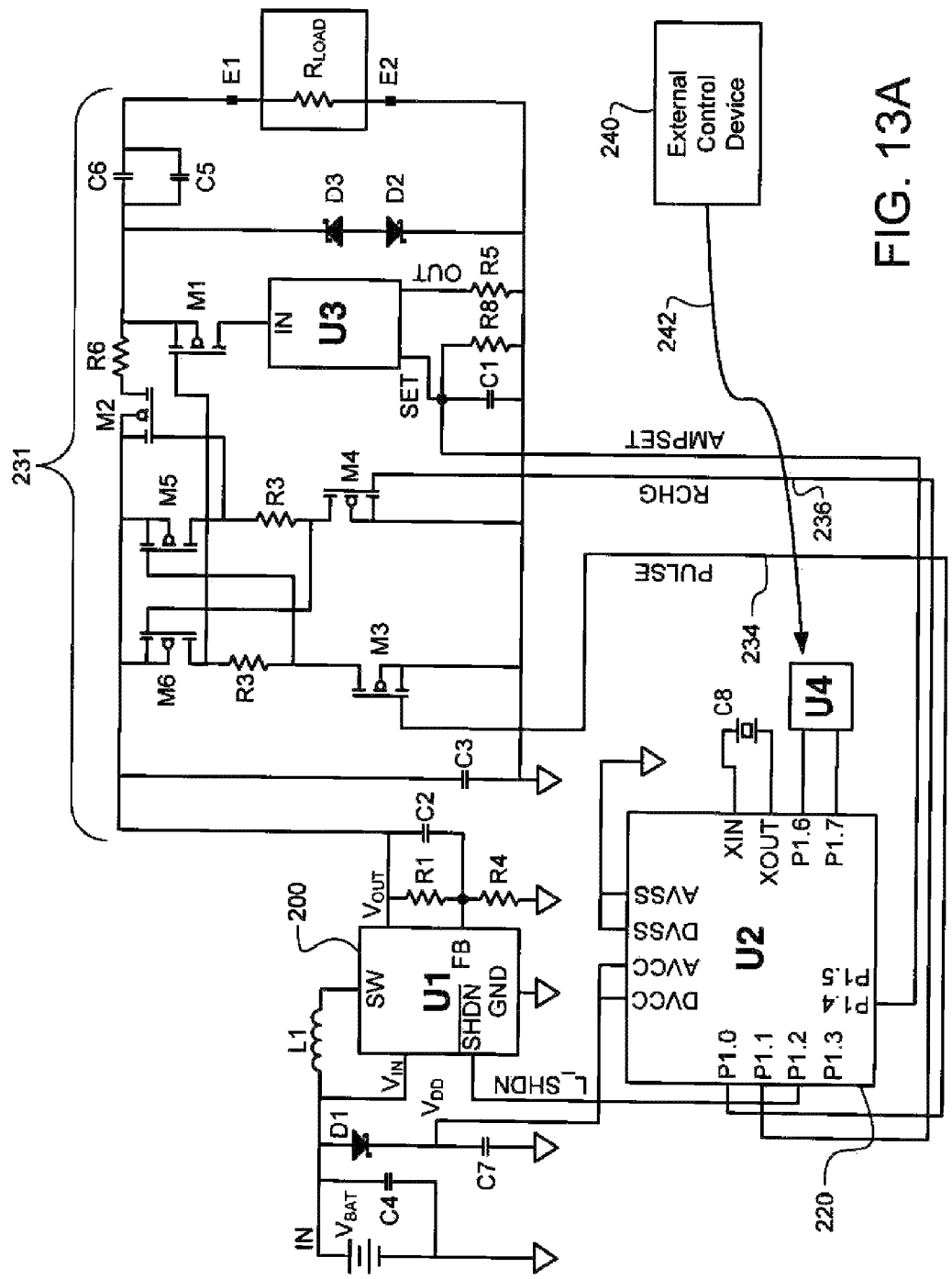
FIG. 13A shows one preferred schematic configuration for an implantable electroacupuncture device (IEAD) that utilizes the boost converter configuration shown in FIG. 10.

One preferred embodiment of the circuitry used in an implantable electroacupuncture device (IEAD) 100 that employs a digital control signal as taught herein is shown in the schematic diagram shown in FIG. 13A. In FIG. 13A, there are basically four integrated circuits (ICs) used as the main components. The IC U1 is a boost converter circuit, and performs the function of the boost converter circuit 200 described previously in connection with FIGS. 8B, 10, 11 and 12.

The IC U2 is a micro-controller IC and is used to perform the function of the control circuit 220 described previously in connection with FIGS. 10, 11 and 12. A preferred IC for this purpose is a MSP430G2452I micro-controller chip made by Texas Instruments. This chip includes 8 KB of Flash memory. Having some memory included with the micro-controller is important because it allows the parameters associated with a selected stimulation regimen to be defined and stored. One of the advantages of the IEAD described herein is that it provides a stimulation regimen that can be defined with just 5 parameters, as taught below in connection with FIGS. 15A and 15B. This allows the programming features of the micro-controller to be carried out in a simple and straightforward manner.

The micro-controller U2 primarily performs the function of generating the digital signal that shuts down the boost converter to prevent too much instantaneous current from being drawn from the battery $V_{BAT}$. The micro-controller U2 also controls the generation of the stimulus pulses at the desired pulse width and frequency. It further keeps track of the time periods associated with a stimulation session, i.e., when a stimulation session begins and when it ends.

The micro-controller U2 also controls the amplitude of the stimulus pulse. This is done by adjusting the value of a current generated by a Programmable Current Source U3. In one embodiment, U3 is realized with a voltage controlled current source IC. In such a voltage controlled current source, the programmed current is set by a programmed voltage appearing across a fixed resistor R5, i.e., the voltage appearing at the "OUT" terminal of U3. This programmed voltage, in turn, is set by the voltage applied to the "SET" terminal of U3. That is, the programmed current source U3 sets the voltage at the "OUT" terminal to be equal to the voltage applied to the "SET" terminal. The programmed current that flows through the resistor R5 is then set by Ohms Law to be the voltage at the "set" terminal divided by R5. As the voltage at the "set" terminal changes, the current flowing through resistor R5 at the "OUT" terminal changes, and this current is essentially the same as the current pulled through the closed switch M1, which is essentially the same current flowing through the load $R_{LOAD}$. Hence, whatever current flows through resistor R5, as set by the voltage across resistor R5, is essentially the same current that flows through the load $R_{LOAD}$. Thus, as the micro-controller U2 sets the voltage at the "set" terminal of U3, on the signal line labeled "AMPSET", it controls what current flows through the load $R_{LOAD}$. In no event can the amplitude of the voltage pulse developed across the load $R_{LOAD}$ exceed the voltage $V_{OUT}$ developed by the boost converter less the voltage drops across the switches and current source.

The switches $S_R$ and $S_P$ described previously in connection with FIGS. 10, 11 and 12 are realized with transistor switches M1, M2, M3, M4, M5 and M6, each of which is controlled directly or indirectly by control signals generated by the micro-controller circuit U2. For the embodiment shown in FIG. 13A, these switches are controlled by two signals, one appearing on signal line 234, labeled PULSE, and the other appearing on signal line 236, labeled RCHG (which is an abbreviation for "recharge"). For the circuit configuration shown in FIG. 13A, the RCHG signal on signal line 236 is always the inverse of the PULSE signal appearing on signal line 234. This type of control does not allow both switch M1 and switch M2 to be open or closed at the same time. Rather, switch M1 is closed when switch M2 is open, and switch M2 is closed, when switch M1 is open. When switch M1 is closed, and switch M2 is open, the stimulus pulse appears across the load, $R_{LOAD}$, with the current flowing through the load, $R_{LOAD}$, being essentially equal to the current flowing through resistor R5. When the switch M1 is open, and switch M2 is closed, no stimulus pulse appears across the load, and the coupling capacitors C5 and C6 are recharged through the closed switch M2 and resistor R6 to the voltage $V_{OUT}$ in anticipation of the next stimulus pulse.

The circuitry shown in FIG. 13A is only exemplary of one type of circuit that may be used to control the pulse width, amplitude, frequency, and duty cycle of stimulation pulses applied to the load, $R_{LOAD}$. Any type of circuit, or control, that allows stimulation pulses of a desired magnitude (measured in terms of pulse width, frequency and amplitude, where the amplitude may be measured in current or voltage) to be applied through the electrodes to the patient at the specified acupoint at a desired duty cycle (stimulation session duration and frequency) may be used. However, for the circuitry to perform its intended function over a long period of time, e.g., years, using only a small energy source, e.g., a small coin-sized battery having a high battery impedance and a relatively low capacity, the circuitry must be properly managed and controlled to prevent excessive current draw from the battery.

It is also important that the circuitry used in the IEAD 100, e.g., the circuitry shown in FIGS. 10, 11, 12, 13A, or equivalents thereof, have some means for controlling the stimulation current that flows through the load, $R_{LOAD}$, which load may be characterized as the patient's tissue impedance at and around the acupoint being stimulated. This tissue impedance, as shown in FIGS. 11 and 12, may typically vary from between about 300 ohms to 2000 ohms. Moreover, it not only varies from one patient to another, but it varies over time. Hence, there is a need to control the current that flows through this variable load, $R_{LOAD}$. One way of accomplishing this goal is to control the stimulation current, as opposed to the stimulation voltage, so that the same current will flow through the tissue load regardless of changes that may occur in the tissue impedance over time. The use of a voltage controlled current source U3, as shown in FIG. 13A, is one way to satisfy this need.

Still referring to FIG. 13A, a fourth IC U4 is connected to the micro-controller U2. For the embodiment shown in FIG. 13A, the IC U4 is a magnetic sensor, and it allows the presence of an externally-generated (non-implanted) magnetic field to be sensed. Such magnetic field is generated using an External Control Device (ECD) 240 that communicates wirelessly, e.g., through the presence or absence of a magnetic field, with the magnetic sensor U4. (A magnetic field is symbolically illustrated in FIG. 13A by the wavy line 242.) In its simplest form, the ECD 240 may simply be a magnet, and modulation of the magnetic field is achieved simply by placing or removing the magnet next to or away from the IEAD.

Use of the ECD 240 provides a way for the patient, or medical personnel, to control the IEAD 100 after it has been implanted (or before it is implanted) with some simple commands, e.g., turn the IEAD ON, turn the IEAD OFF, increase the amplitude of the stimulation pulses by one increment, decrease the amplitude of the stimulation pulses by one increment, and the like. A simple coding scheme may be used to differentiate one command from another. For example, one coding scheme is time-based. That is, a first command is communicated by holding a magnet near the IEAD 100, and hence near the magnetic sensor U4 contained within the IEAD 100, for differing lengths of time. If, for example, a magnet is held over the IEAD for at least 2 seconds, but no more than 7 seconds, a first command is communicated. If a magnet is held over the IEAD for at least 11 seconds, but no more than 18 seconds, a second command is communicated, and so forth.

Another coding scheme that could be used is a sequence-based coding scheme. That is, application of 3 magnetic pulses may be used to signal one external command, if the sequence is repeated 3 times. A sequence of 2 magnetic pulses, repeated twice, may be used to signal another external command. A sequence of one magnetic pulse, followed by a sequence of two magnetic pulses, followed by a sequence of three magnetic pulses, may be used to signal yet another external command.

Other simple coding schemes may also be used, such as the letters AA, RR, HO, BT, KS using international Morse code. That is, the Morse code symbols for the letter "A" are dot dash, where a dot is a short magnetic pulse, and a dash is a long magnetic pulse. Thus, to send the letter A to the IEAD 100 using an external magnet, the user would hold the magnet over the area where the IEAD 100 is implanted for a short period of time, e.g., one second or less, followed by holding the magnet over the IEAD for a long period of time, e.g., more than one second.

More sophisticated magnetic coding schemes may be used to communicate to the micro-controller chip U2 the operating parameters of the IEAD 100. For example, using an electromagnet controlled by a computer, the pulse width, frequency, and amplitude of the EA stimulation pulses used during each stimulation session may be pre-set. Also, the frequency of the stimulation sessions can be pre-set. Additionally, a master reset signal can be sent to the device in order to re-set these parameters to default values. These same operating parameters and commands may be re-sent at any time to the IEAD 100 during its useful lifetime should changes in the parameters be desired or needed.

Figure 13B:
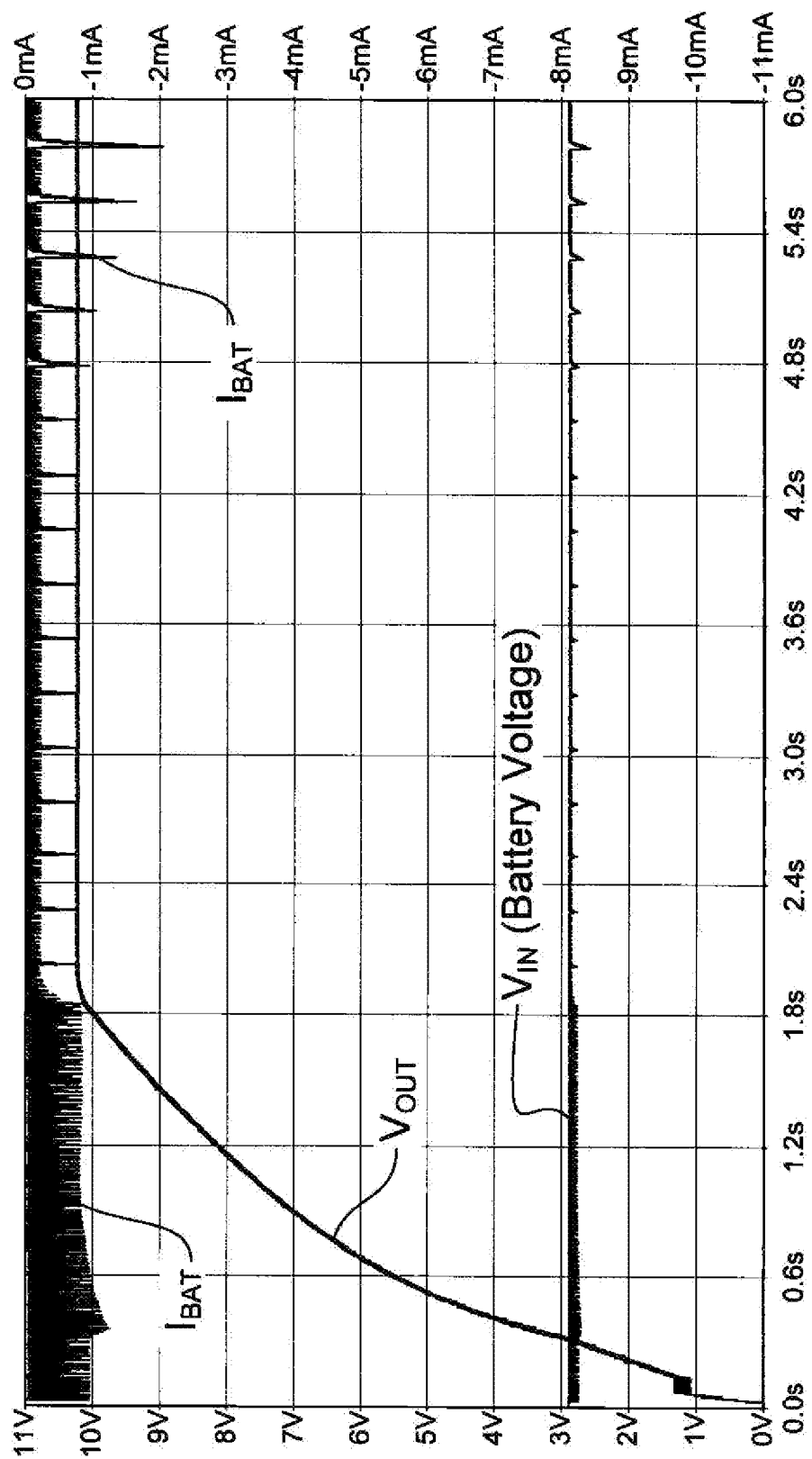
FIG. 13B shows current and voltage waveforms associated with the operation of the circuit shown in FIG. 13A.

The current and voltage waveforms associated with the operation of the IEAD circuitry of FIG. 13A are shown in FIG. 13B. In FIG. 13B, the horizontal axis is time, the left vertical axis is voltage, and the right vertical axis is current. The battery in this example has 160 Ohms of internal impedance.

Referring to FIGS. 13A and 13B, during startup, the boost converter ON time is approximately 30 microseconds applied every 7.8 milliseconds. This is sufficient to ramp the output voltage $V_{OUT}$ up to over 10 V within 2 seconds while drawing no more than about 1 mA from the battery and inducing only 150 mV of input voltage ripple.

The electroacupuncture (EA) simulation pulses resulting from operation of the circuit of FIG. 13 have a width of 0.5 milliseconds and increase in amplitude from approximately 1 mA in the first pulse to approximately 15 mA in the last pulse. The instantaneous current drawn from the battery is less than 2 mA for the EA pulses and the drop in battery voltage is less than approximately 300 mV. The boost converter is enabled (turned ON) only during the instantaneous output current surges associated with the 0.5 milliseconds wide EA pulses.

Figure 14:
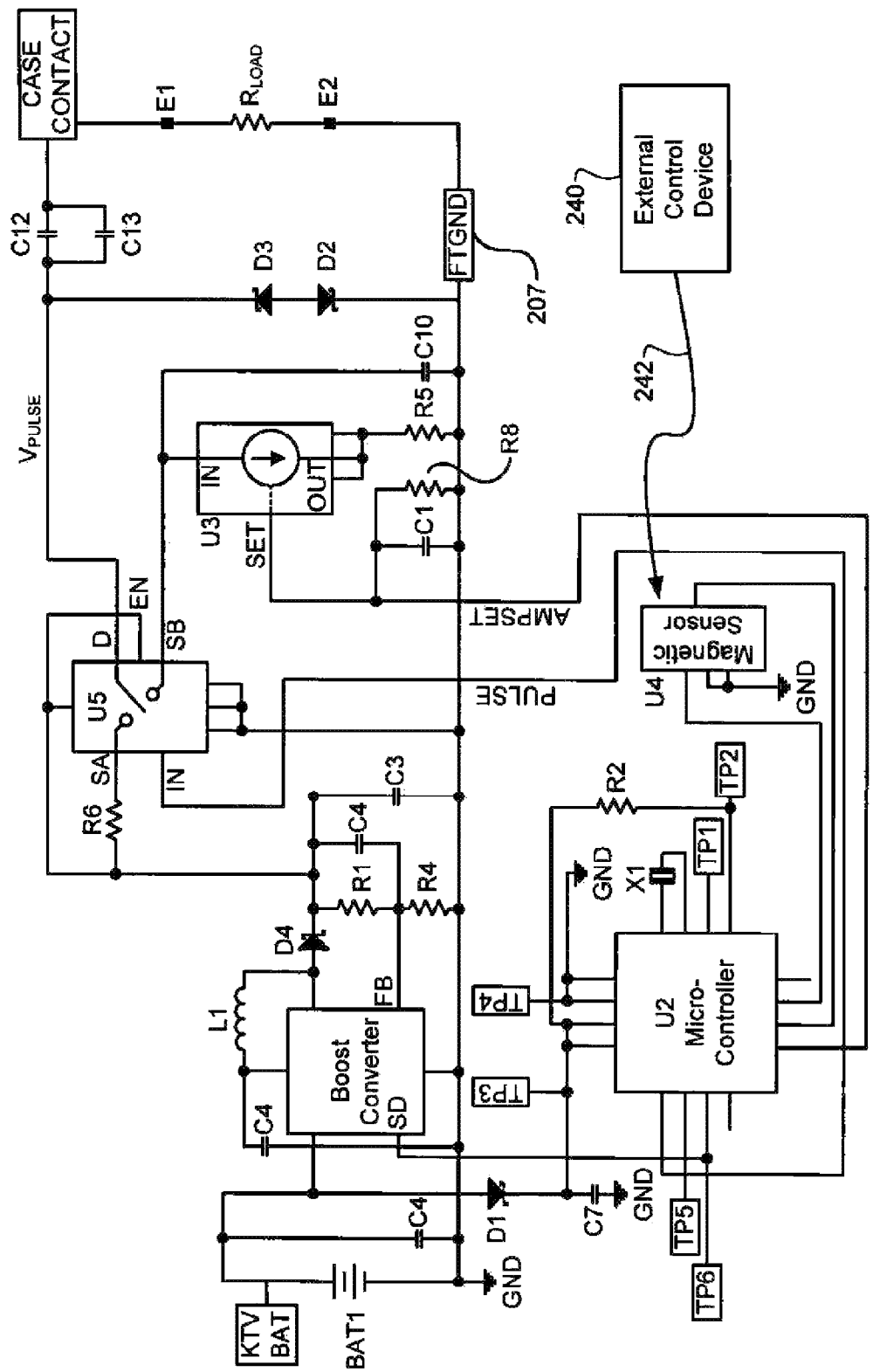
FIG. 14 shows another preferred schematic configuration for an IEAD similar to that shown in FIG. 13A, but which uses an alternate output circuitry configuration for generating the stimulus pulses.

Another preferred embodiment of the circuitry used in an implantable electroacupuncture device (IEAD) 100 that employs a digital control signal as taught herein is shown in the schematic diagram of FIG. 14. The circuit shown in FIG. 14 is, in most respects, very similar to the circuit described previously in connection with FIG. 13A. What is new in FIG. 14 is the inclusion of an external Schottky diode D4 at the output terminal LX of the boost convertor U1 and the inclusion of a fifth integrated circuit (IC) U5 that essentially performs the same function as the switches M1-M6 shown in FIG. 13A.

The Schottky diode D5 helps isolate the output voltage $V_{OUT}$ generated by the boost converter circuit U1. This is important in applications where the boost converter circuit U1 is selected and operated to provide an output voltage $V_{OUT}$ that is four or five times as great as the battery voltage, $V_{BAT}$. For example, in the embodiment for which the circuit of FIG. 14 is designed, the output voltage $V_{OUT}$ is designed to be nominally 15 volts using a battery that has a nominal battery voltage of only 3 volts. (In contrast, the embodiment shown in FIG. 13A is designed to provide an output voltage that is nominally 10-12 volts, using a battery having a nominal output voltage of 3 volts.)

The inclusion of the fifth IC U5 in the circuit shown in FIG. 14 is, as indicated, used to perform the function of a switch. The other ICs shown in FIG. 14, U1 (boost converter), U2 (micro-controller), U3 (voltage controlled programmable current source) and U4 (magnetic sensor) are basically the same as the IC's U1, U2, U3 and U4 described previously in connection with FIG. 13A.

The IC U5 shown in FIG. 14 functions as a single pole/double throw (SPDT) switch. Numerous commercially-available ICs may be used for this function. For example, an ADG1419 IC, available from Analog Devices Incorporated (ADI) may be used. In such IC U5, the terminal "D" functions as the common terminal of the switch, and the terminals "SA" and "SB" function as the selected output terminal of the switch. The terminals "IN" and "EN" are control terminals to control the position of the switch. Thus, when there is a signal present on the PULSE line, which is connected to the "IN" terminal of U5, the SPDT switch U5 connects the "D" terminal to the "SB" terminal, and the SPDT switch U5 effectively connects the cathode electrode E1 to the programmable current source U3. This connection thus causes the programmed current, set by the control voltage AMPSET applied to the SET terminal of the programmable current source U3, to flow through resistor R5, which in turn causes essentially the same current to flow through the load, $R_{LOAD}$, present between the electrodes E1 and E2. When a signal is not present on the PULSE line, the SPDT switch U5 effectively connects the cathode electrode E1 to the resistor R6, which allows the coupling capacitors C12 and C13 to recharge back to the voltage $V_{OUT}$ provided by the boost converter circuit U2.

From the above description, it is seen that an implantable IEAD 100 is provided that uses a digital control signal to duty-cycle limit the instantaneous current drawn from the battery by a boost converter. Three different exemplary configurations (FIGS. 10, 11 and 12) are taught for achieving this desired result, and two exemplary circuit designs that may be used to realize this result have been disclosed (FIGS. 13A and 14). One configuration (FIG. 12) teaches the additional capability to delta-sigma modulate the boost converter output voltage.

Delta-sigma modulation is well described in the art. Basically, it is a method for encoding analog signals into digital signals or higher-resolution digital signals into lower-resolution digital signals. The conversion is done using error feedback, where the difference between the two signals is measured and used to improve the conversion. The low-resolution signal typically changes more quickly than the high-resolution signal and it can be filtered to recover the high resolution signal with little or no loss of fidelity. Delta-sigma modulation has found increasing use in modern electronic components such as converters, frequency synthesizers, switched-mode power supplies and motor controllers. See, e.g., Wikipedia, Delta-sigma modulation.

Use and Operation

With the implantable electroacupuncture device (IEAD) 100 in hand, the IEAD 100 may be used most effectively to treat hypertension by first pre-setting stimulation parameters that the device will use during a stimulation session. FIG. 15A shows a timing waveform diagram illustrating the EA stimulation parameters used by the IEAD to generate EA stimulation pulses. As seen in FIG. 15A, there are basically four parameters associated with a stimulation session. The time T1 defines the duration (or pulse width) of a stimulus pulse. The time T2 defines the time between the start of one stimulus pulse and the start of the next stimulus pulse. The time T2 thus defines the period associated with the frequency of the stimulus pulses. The frequency of the stimulation pulses is equal to 1/T2. The ratio of T1/T2 is typically quite low, e.g., less than 0.01. The duration of a stimulation session is defined by the time period T3. The amplitude of the stimulus pulses is defined by the amplitude A1. This amplitude may be expressed in either voltage or current.

Figure 15B:
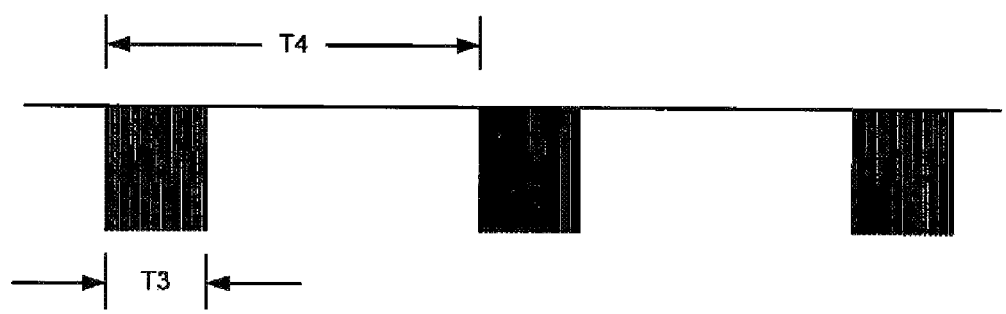
FIG. 15B shows a timing waveform diagram of multiple stimulation sessions, and illustrates the waveforms on a more condensed time scale.

Turning next to FIG. 15B, a timing waveform diagram is shown that illustrates the manner in which the stimulation sessions are administered in accordance with a preferred stimulation regimen. FIG. 15B shows several stimulation sessions of duration T3, and how often the stimulation sessions occur. The stimulation regimen thus includes a time period T4 which sets the time period from the start of one stimulation session to the start of the next stimulation session. The time period T4 is thus the period of the stimulation session frequency, and the stimulation session frequency is equal to 1/T4.

By way of example, one set of parameters that could be used to define a stimulation regimen is T1=0.5 milliseconds
T2=500 milliseconds
T3=30 minutes
T4=7 days (10,080 minutes)
A1=6 volts (across 1 kOhm), or 6 milliamperes (mA)

It is to be emphasized that the values shown above for the stimulation regimen are representative of only one preferred stimulation regimen that could be used. Other stimulation regimens that could be used, and the ranges of values that could be used for each of these parameters, are as defined in the claims.

It is also emphasized that the ranges of values presented in the claims for the parameters used with the invention have been selected after many months of careful research and study, and are not arbitrary. For example, the ratio of T3/T4, which sets the duty cycle, has been carefully selected to be very low, e.g., no more than 0.05. Maintaining a low duty cycle of this magnitude represents a significant change over what others have attempted in the implantable stimulator art. Not only does a very low duty cycle allow the battery itself to be small (coin cell size), which in turn allows the IEAD housing to be very small, which makes the IEAD ideally suited for being used without leads, thereby making it relatively easy to implant the device at the desired acupuncture site, but it also limits the frequency and duration of stimulation sessions. Limiting the frequency and duration of the stimulation sessions is a key aspect of Applicant's invention because it recognizes that some treatments, such as treating hypertension, are best done slowly and methodically, over time, rather than quickly and harshly using large doses of stimulation (or other treatments) aimed at forcing a rapid change in the patient's condition. Moreover, applying treatments slowly and methodically is more in keeping with traditional acupuncture methods (which, as indicated previously, are based on over 2500 years of experience). Thus, Applicant has based its treatment regimens on the slow-and-methodical approach, as opposed to the immediate-and-forced approach adopted by many, if not most, prior art implantable electrical stimulators.

Once the stimulation regimen has been defined and the parameters associated with it have been pre-set into the memory of the micro-controller circuit 220, the IEAD 100 needs to be implanted. Implantation is a simple procedure, and is described above in connection with the description of FIGS. 1A and 1B.

For treating the specific conditions of cardiovascular disease targeted by this embodiment of the invention, i.e., heart failure, CAD, myocardial ischemia or angina, the specified acupoint at which the EA stimulation pulses should be applied in accordance with a selected stimulation regimen is, for purposes of the invention described and claimed herein, PC6 in the right and/or left wrist (or forearm) of the patient. Alternatively, the stimulation pulses may be applied at a point near PC6, such as a point along the axis line between PC6 and an adjoining acupoint (e.g., PC5 or PC7). Further, it is noted that EA stimulation applied at or near PC6 may be applied unilaterally (an IEAD in just one forearm) or bilaterally (an IEAD in both forearms).

Figure 16:
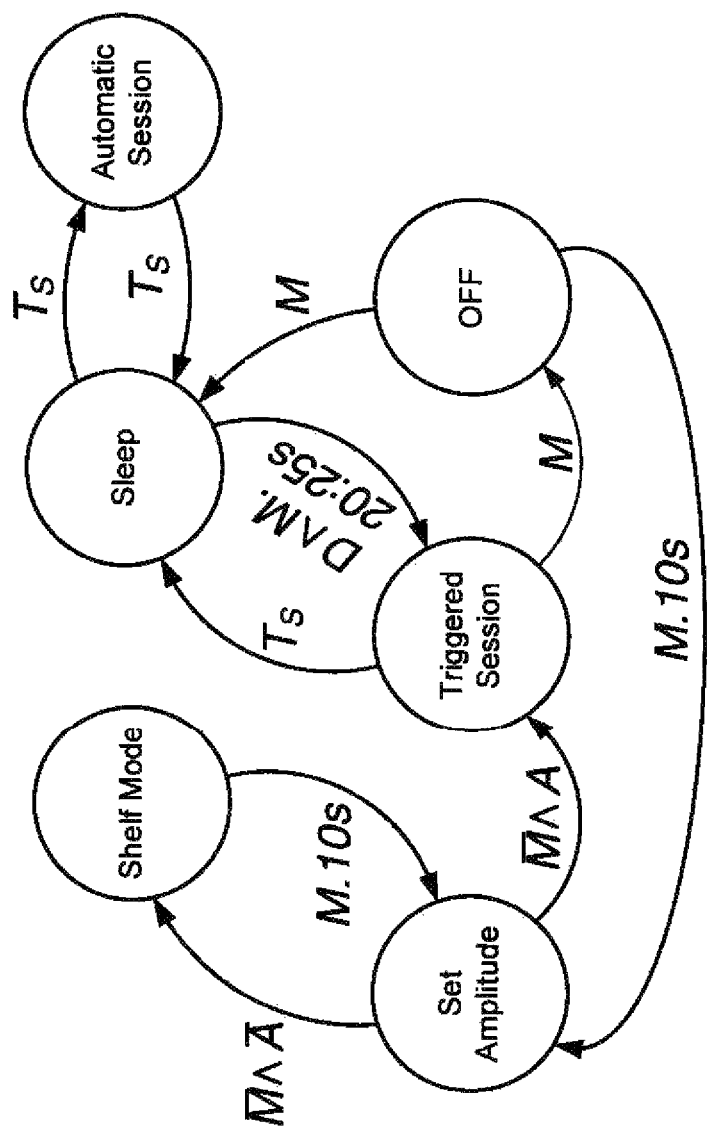
FIG. 16 shows a state diagram that shows the various states in which the IEAD may be placed through the use of an external magnet.

After implantation, the IEAD must be turned ON, and otherwise controlled, so that the desired stimulation regimen may be carried out. In one preferred embodiment, control of the IEAD after implantation, as well as anytime after the housing of the IEAD has been hermetically sealed, is performed as shown in the state diagram of FIG. 16. Each circle shown in FIG. 16 represents a "state" that the micro-controller U2 (in FIG. 13A or 14) may operate in under the conditions specified. As seen in FIG. 16, the controller U2 only operates in one of six states: (1) a "Set Amplitude" state, (2) a "Shelf Mode" state, (3) a "Triggered Session" state, (4) a "Sleep" state, (5) an "OFF" state, and an (6) "Automatic Session" state. The "Automatic Session" state is the state that automatically carries out the stimulation regimen using the pre-programmed parameters that define the stimulation regimen.

Shelf Mode is a low power state in which the IEAD is placed prior to shipment. After implant, commands are made through magnet application. Magnet application means an external magnet, typically a small hand-held cylindrical magnet, is placed over the location where the IEAD has been implanted. With a magnet in that location, the magnetic sensor U4 senses the presence of the magnet and notifies the controller U2 of the magnet's presence.

From the "Shelf Mode" state, a magnet application for 10 seconds (M.10s) puts the IEAD in the "Set Amplitude" state. While in the "Set Amplitude" state, the stimulation starts running by generating pulses at zero amplitude, incrementing every five seconds until the patient indicates that a comfortable level has been reached. At that time, the magnet is removed to set the amplitude.

If the magnet is removed and the amplitude is non-zero ($\overline{M}A\overline{A}$), the device continues into the "Triggered Session" so the patient receives the initial therapy. If the magnet is removed during "Set Amplitude" while the amplitude is zero ($\overline{M}A\overline{A}$), the device returns to the Shelf Mode.

The Triggered Session ends and stimulation stops after the session time ($T_S$) has elapsed and the device enters the "Sleep" state. If a magnet is applied during a Triggered Session (M), the session aborts to the "OFF" state. If the magnet remains held on for 10 seconds (M.10s) while in the "OFF" state, the "Set Amplitude" state is entered with the stimulation level starting from zero amplitude as described.

If the magnet is removed ($\overline{M}$) within 10 seconds while in the OFF state, the device enters the Sleep state. From the Sleep state, the device automatically enters the Automatic Session state when the session interval time has expired ($T_I$). The Automatic Session delivers stimulation for the session time ($T_S$) and the device returns to the Sleep state. In this embodiment, the magnet has no effect once the Automatic Session starts so that the full therapy session is delivered.

While in the Sleep state, if a magnet has not been applied in the last 30 seconds (D) and a magnet is applied for a window between 20-25 seconds and then removed (M.20:25s), a Triggered Session is started. If the magnet window is missed (i.e. magnet removed too soon or too late), the 30 second de-bounce period (D) is started. When de-bounce is active, no magnet must be detected for 30 seconds before a Triggered Session can be initiated.

The session interval timer runs while the device is in Sleep state. The session interval timer is initialized when the device is woken up from Shelf Mode and is reset after each session is completely delivered. Thus abort of a triggered session by magnet application will not reset the timer, the Triggered Session must be completely delivered.

The circuitry that sets the various states shown in FIG. 16 as a function of externally-generated magnetic control commands, or other externally-generated command signals, is the micro-controller U2 (FIG. 14), the processor U2 (FIG. 13A), or the control circuit 220 (FIGS. 10, 11 and 12). Such processor-type circuits are programmable circuits that operate as directed by a program. The program is often referred to as "code", or a sequence of steps that the processor circuit follows. The "code" can take many forms, and be written in many different languages and formats, known to those of skill in the art. Representative "code" for the micro-controller U2 (FIG. 14) for controlling the states of the IEAD as shown in FIG. 16 is found in Appendix C, attached hereto, and incorporated by reference herein.

Relationship with Applicant's Other Inventions

Readers of this patent application who have also read Applicant's copending patent application(s) relating to the treatment of hypertension using a small, implantable EA device of the type described herein, will recognize that the treatment described there for hypertension treatment, including one of the acupoints, PC6, where the stimulation pulses are applied, is essentially the same as that described herein for the treatment of the four conditions of cardiovascular disease (heart failure, CAD, myocardial ischemia and angina) that are the focus of this patent application. Why is this? Are the inventions the same invention? The answer is that while the apparatus (the small implantable EA device) is essentially the same, and the stimulation regimen and point of application are essentially the same (or at least potentially may be the same depending upon the particular acupoint selected and the particular stimulation regimen parameters selected), the inventions target different conditions, and hence are different. Just like a wrench, for example, is a tool that may be used, sometimes alone but most often in combination with other tools, for a wide variety of applications, the EA device described herein, and its manner of use, may be used, sometimes alone but most often in combination with other tools, for a wide variety of beneficial applications, one of which is treating various conditions associated with cardiovascular disease, and another of which is treating hypertension.

The close relationship between the two inventions (hypertension treatment and cardiovascular disease treatement) makes sense. In addition to heart failure, the sympaththetic nervous system (SNS) is increased in the other conditions Applicant treats with this invention—in coronary artery disease, angina, and myocardial ischemia. Raised sympathetic nervous activity is the common denominator. And while a patient with one of these aforementioned conditions may or may not be hypertensive, the mechanism of action brought about by the device and methods disclosed in Applicant's hypertension treatment patent application involves the reduction of sympathetic activity. That is, the effect on blood pressure, Appplicant submits, from the use of their EA device at acupoint PC6 (Neiguan), is secondary and results from the inhibiting effect on the SNS.

For example, in experimental models, it has been demonstrated that low frequency electroacupuncture (EA) stimulation at acupoint PC6 (Neiguan) effectively stimulates somatic afferents to provide input to regions such as the rVLM that regulates sympathetic outflow. See, Zhou W Y, Tjen-A-Looi S C, Longhurst J C, "Brain stem mechanisms underlying acupuncture modality-related modulation of cardiovascular responses in rats," *J Appl Physiol* 2005, 99:851-860; Zhou W, Fu L W, Tjen-A-Looi S C, et al., "Afferent mechanisms underlying stimulation of modality-related modulation of acupuncture-related cardiovascular responses," *J Appl Physiol* 2005, 98:872-880. Furthermore, in experiments measuring the effect of stimulating acupoint PC6 (Neiguan) on blood pressure, the extent of blood pressure depression is dependent on the extent of convergent input to premotor sympathetic neurons in the rVLM. Tjen-A-Looi S C, Li P, Longhurst J C. "Medullary substrate and differential cardiovascular responses during stimulation of specific acupoints," *Am J Physiol Regul Integr Comp Physiol* 2004, 287:R852-R862. Thus, the effect on blood pressure seems to follow the effect on sympathetic activity.

Since Applicant believes the stimulation regimen and target at PC6 (Neiguan) disclosed in its hypertension treatment patent application represents at least one optimal system for reducing sympathetic activity, it has chosen to apply the same system to the conditions disclosed herein for which raised sympathetic activation is problematic. In fact, while much of the acupuncture studies performed at acupoint PC6 (Neiguan) were done to treat hypertension, the mechanism by which Applicant believes hypertension is improved—the reduction of sympathetic activity—may be more central to the treatment of heart failure. That is, hypertension may not always be driven sympathetically, whereas the hallmark of heart failure is heightened sympathetic drive. Thus, it is important that Applicant targets the SNS in the treatment of heart failure, in particular, by the application of its EA device at acupoint PC6 (Neiguan).

In the preceding description, various exemplary embodiments have been described with reference to the accompanying drawings. It will, however, be evident that various modifications and changes may be made thereto, and additional embodiments may be implemented, without departing from the scope of the invention as set forth in the claims that follow. For example, certain features of one embodiment described herein may be combined with or substituted for features of another embodiment described herein. The description and drawings are accordingly to be regarded in an illustrative rather than a restrictive sense.

Further, the preceding description has been presented only to illustrate and describe some embodiments of the invention. It is not intended to be exhaustive or to limit the invention to any precise form disclosed. Many modifications and variations are possible in light of the above teaching. Thus, while the invention(s) herein disclosed has been described by means of specific embodiments and applications thereof, numerous modifications and variations could be made thereto by those skilled in the art without departing from the scope of the invention(s) set forth in the claims.

What is claimed is:

1. A method of treating cardiovascular disease in a patient using a small, leadless, implantable electroacupuncture device (IEAD) powered by a small disc primary battery having a specified nominal output voltage of 3 volts, and having an internal impedance of at least 5 ohms, the IEAD being configured, using electronic circuitry within the IEAD, to generate electroacupuncture (EA) stimulation pulses in accordance with a specified stimulation regimen and apply the EA stimulation pulses through at least two electrodes/arrays located on the housing of the IEAD to the patient's body tissue at a selected tissue location, said at least two electrodes/arrays comprising at least one central electrode/array of a first polarity, having a maximum width of no more 7 mm, centrally located on a first surface of the small IEAD housing, and at least one annular electrode/array of a second polarity spaced apart from the central electrode/array by at least 5 mm measured from the edge of the annular electrode/array closest to the central electrode/array to the center of the central electrode/array, said method comprising:

(a) implanting the IEAD below the skin surface of the patient at one or more acupoints selected from the group of acupoints comprising PC6, or a point along an axis line connecting point PC6 with PC5 or PC7, with the first surface of the IEAD facing inwardly into the patient's body tissue at the selected acupoint;

(b) enabling the IEAD to provide stimulation pulses in accordance with a stimulation regimen that provides a stimulation session at a rate of once every T4 minutes, with each stimulation session having a duration of T3 minutes, where the ratio of T3/T4 is no greater than 0.05.

2. The method of claim 1 further including setting the time T4 to be at least 720 minutes [½ day], but no more than about 20,160 minutes [14 days].

3. The method of claim 2 further setting T3, the duration of the stimulation session, to a value between 10 minutes and 60 minutes if T4, the rate of occurrence of the stimulation session, is set to a value between 1,200 minutes and 20,160 minutes [14 days]; and setting T3 to a value between 10 minutes and a maximum T3 value, T3(max), if T4 is set to a value between 720 minutes and 1,200 minutes, wherein T3(max) varies as a function of T4 as defined by the equation:

$$T3(\max)=0.05*T4.$$

4. The method of claim 2 further including setting the stimulation pulses during a stimulation session to have a duration of T1 seconds, that occur at a rate of once every T2 seconds, where the ratio of T1/T2 is no greater than 0.01.

5. The method of claim 4 further including setting the time T1 to be 0.1 to 1.0 millisecond and the time T2 to be 250 to 1000 milliseconds.

6. The method of claim 1 further including controlling the electronic circuits within the IEAD to limit instantaneous current drawn from the small disc primary battery so that the output voltage of the primary battery does not drop more than about 11% below the output voltage of the primary battery when current is being drawn from the primary battery, where the output voltage of the primary battery is equal to the specified nominal output voltage of the primary battery less the voltage drop caused by the instantaneous current flowing through the internal impedance of the primary battery.

7. The method of claim 6 wherein the electronic circuitry within the IEAD includes a boost converter circuit, and wherein the method of controlling the electronic circuits within the IEAD to limit the instantaneous current drawn from the battery comprises modulating the operation of the boost converter circuit between an ON state and an OFF state.

* * * * *

UNITED STATES PATENT AND TRADEMARK OFFICE
CERTIFICATE OF CORRECTION

PATENT NO.        : 8,938,297 B2
APPLICATION NO.   : 13/622497
DATED             : January 20, 2015
INVENTOR(S)       : Jeffrey H. Greiner et al.

It is certified that error appears in the above-identified patent and that said Letters Patent is hereby corrected as shown below:

On the Title Page, item (57) Abstract, Line 4, replace "acupoints GV20 and/or EXHN3" with --acupoint PC6, or a point along an axis line connecting point PC6 with PC5 or PC7--.

Signed and Sealed this
Twenty-fifth Day of August, 2015

Michelle K. Lee
*Director of the United States Patent and Trademark Office*